United States Patent
Mosher et al.

(10) Patent No.: US 7,315,762 B2
(45) Date of Patent: *Jan. 1, 2008

(54) NON-SURGICAL INCONTINENCE TREATMENT SYSTEM AND METHOD

(75) Inventors: Oren A. Mosher, Castro Valley, CA (US); Carine Hoarau, Pleasant Hill, CA (US); Abdul M. Tayeb, San Leandro, CA (US); George L. Matlock, Pleasanton, CA (US); Daniel D. Merrick, Dublin, CA (US); Terry E. Spraker, Portola Valley, CA (US)

(73) Assignee: American Medical Systems, Inc., Minnetonka, MN (US)

( * ) Notice: Subject to any disclaimer, the term of this patent is extended or adjusted under 35 U.S.C. 154(b) by 333 days.

This patent is subject to a terminal disclaimer.

(21) Appl. No.: 10/759,732

(22) Filed: Jan. 15, 2004

(65) Prior Publication Data

US 2004/0193238 A1 Sep. 30, 2004

Related U.S. Application Data

(60) Provisional application No. 60/440,711, filed on Jan. 16, 2003.

(51) Int. Cl.
*A61F 7/12* (2006.01)
(52) U.S. Cl. ............... 607/99; 607/113; 128/898
(58) Field of Classification Search ............ 606/27–31, 606/40–42, 46; 607/96–114, 138; 128/898
See application file for complete search history.

(56) References Cited

U.S. PATENT DOCUMENTS

| | | | |
|---|---|---|---|
| 5,370,675 A | 12/1994 | Edwards et al. | |
| 5,957,920 A | 9/1999 | Baker | |
| 6,044,846 A | 4/2000 | Edwards | |
| 6,091,995 A * | 7/2000 | Ingle et al. | 607/138 |
| 6,139,569 A | 10/2000 | Ingle et al. | |
| 6,156,060 A * | 12/2000 | Roy et al. | 607/113 |
| 6,197,022 B1 | 3/2001 | Baker | |
| 6,216,704 B1 * | 4/2001 | Ingle et al. | 128/898 |
| 6,283,987 B1 | 9/2001 | Laird et al. | |
| 6,292,700 B1 | 9/2001 | Morrison et al. | |
| 6,325,798 B1 | 12/2001 | Edwards et al. | |
| 6,685,623 B2 * | 2/2004 | Presthus et al. | 600/29 |
| 2003/0144576 A1 | 7/2003 | Presthus et al. | |
| 2003/0181965 A1 | 9/2003 | Levy, Jr. et al. | |
| 2004/0024433 A1 | 2/2004 | Roy et al. | |

OTHER PUBLICATIONS

U.S. Appl. No. 60/022,790, filed Jul. 30, 1996, Baker.
U.S. Appl. No. 60/024,974, filed Aug. 30, 1996, Baker.

* cited by examiner

*Primary Examiner*—Roy D. Gibson
(74) *Attorney, Agent, or Firm*—Adam P. Kiedrowski; Oppenheimer, Wolff & Donnelly; Jose Jimenez

(57) ABSTRACT

Devices, systems, and methods can treat incontinence by heating between about 100 and about 800 cubic millimeters of endopelvic fascia for sufficient time to effect substantial collagenous tissue shrinkage. A probe body may directly engage the endopelvic fascia, or may be separated from the endopelvic fascia, heating through (for example) the vaginal wall. In either case, tissue-penetrating electrodes may be inserted from the probe body so as to heat the endopelvic fascia.

20 Claims, 27 Drawing Sheets

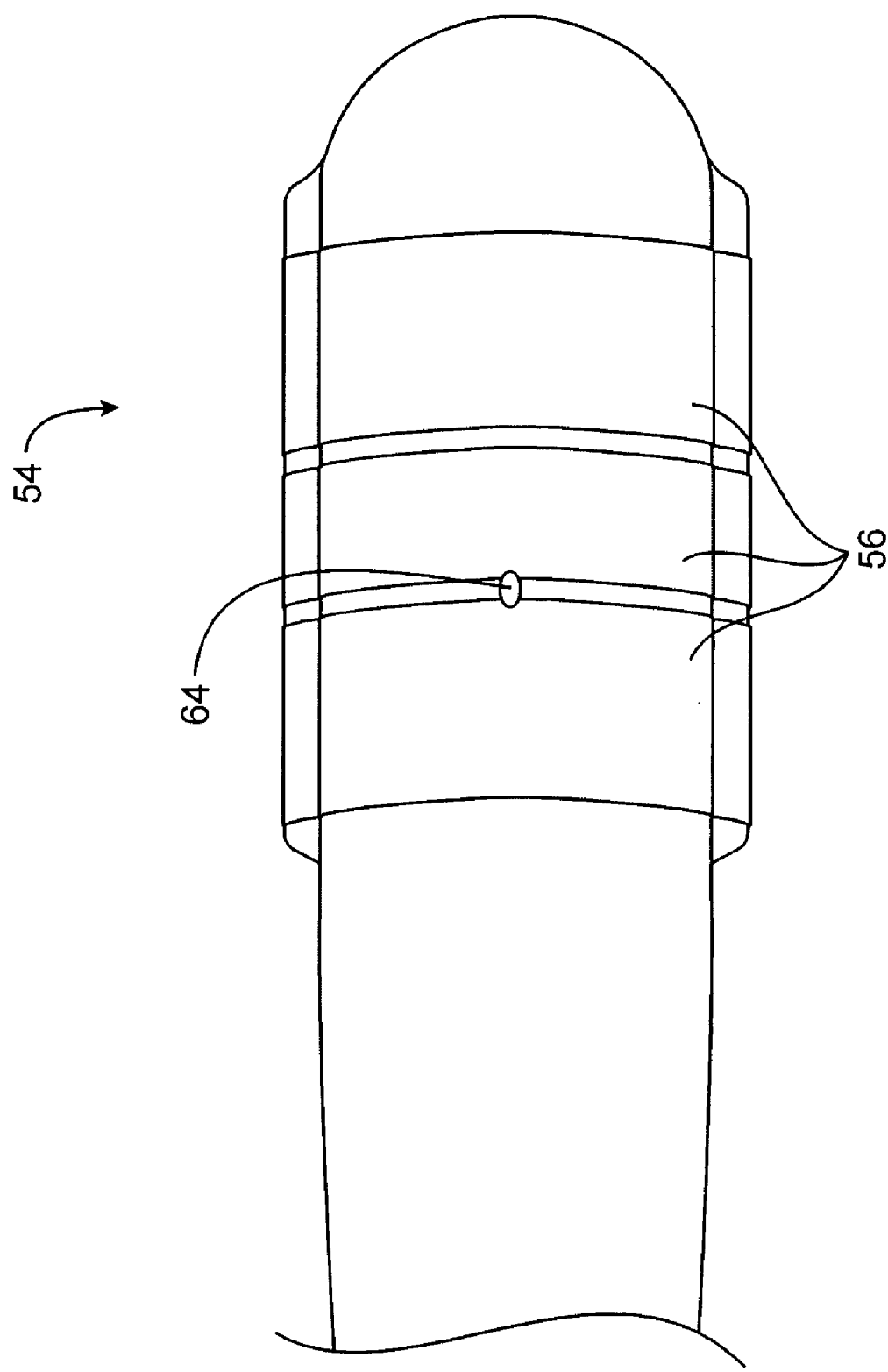

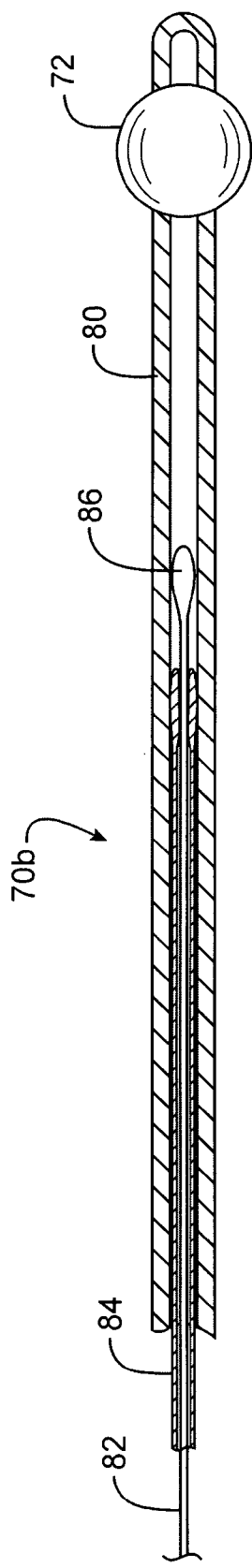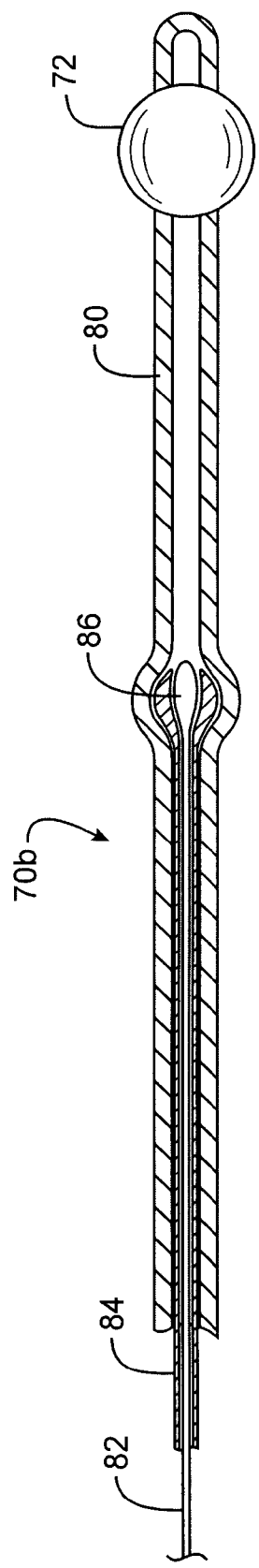
FIG. 7B
FIG. 7C

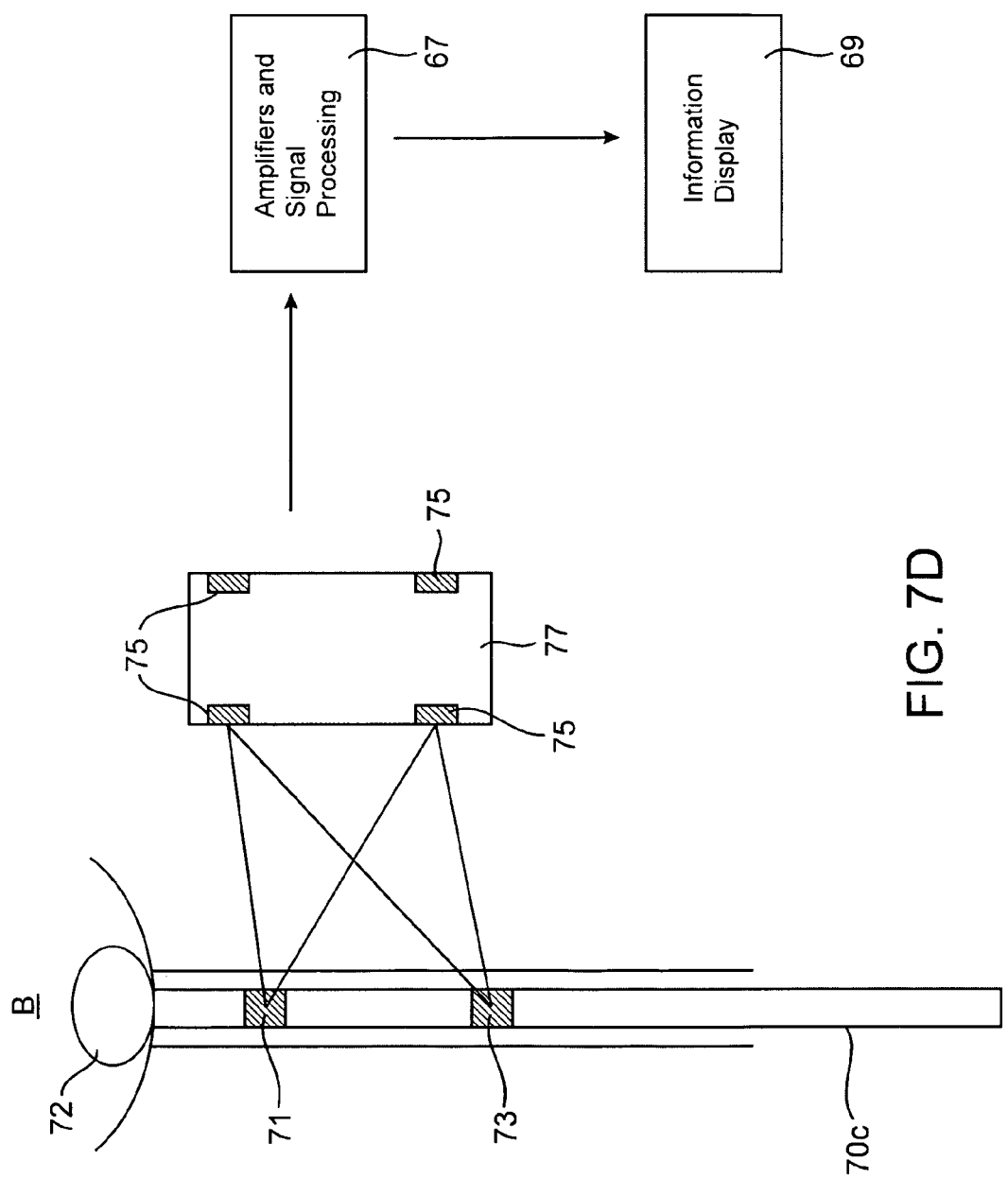

Other Thermal Effects on "Tissue"

| Time (Seconds) | Necrosis (°C) |
|---|---|
| 1 | 54.3 |
| 10 | 51.5 |
| 25 | 50.5 |
| 50 | 50 |
| 75 | 49 |
| 100 | 48.3 |

Collagenated Tissue Mean Shrinkage
65°C, 70°C, 75°C, 80°C, and 85°C

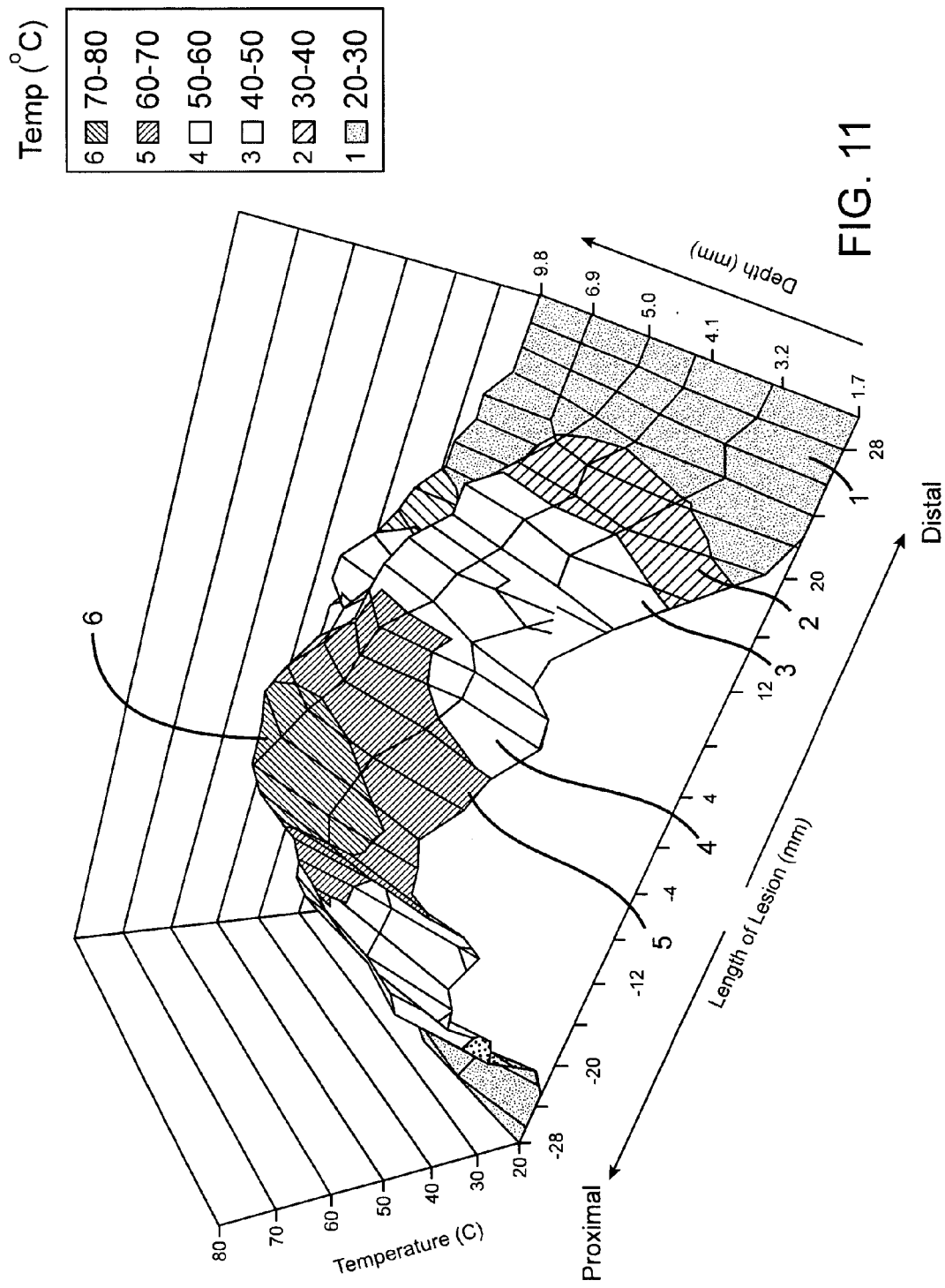

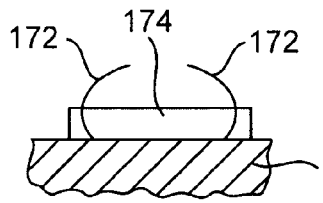
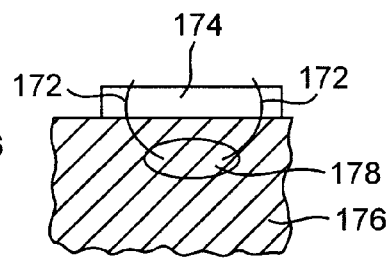
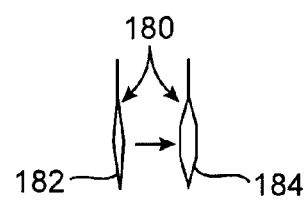
FIG. 21A   FIG. 21B   FIG. 21C
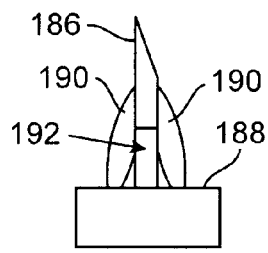
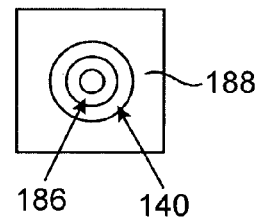
FIG. 22A   FIG. 22B
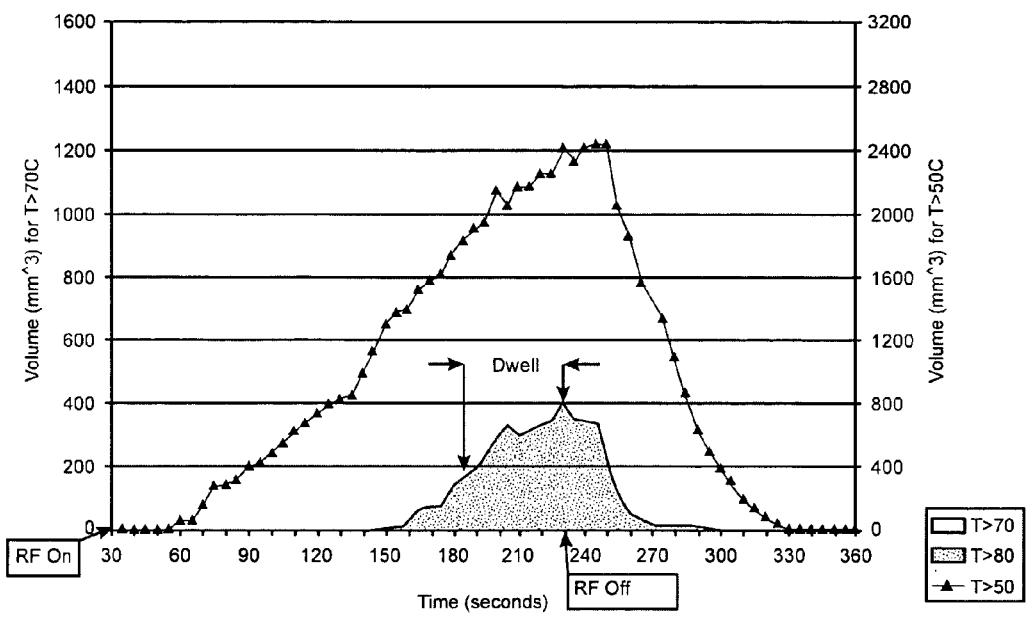
FIG. 23

NON-SURGICAL INCONTINENCE TREATMENT SYSTEM AND METHOD

CROSS-REFERENCES TO RELATED APPLICATIONS

This application claims the benefit priority from U.S. Provisional Patent Application No. 60/440,711, filed Jan. 16, 2003, the full disclosure of which is incorporated herein by reference.

BACKGROUND OF THE INVENTION

Field of the Invention

The present invention generally relates to medical devices, methods, and systems, particularly for the treatment of urinary incontinence.

Urinary incontinence arises in both men and women with varying degrees of severity, and from different causes. In men, the condition frequently occurs as a result of prostatectomies which result in mechanical damage to the urinary sphincter. In women, the condition typically arises after pregnancy when musculoskeletal damage has occurred as a result of inelastic stretching of the structures supporting the genitourinary tract. Specifically, pregnancy can result in inelastic stretching of the pelvic floor, the external sphincter, and the tissue structures which support the bladder, urethra, and bladder neck region. In each of these cases, urinary leakage typically occurs when a patient's abdominal pressure increases as a result of stress, e.g., coughing, sneezing, laughing, exercise, or the like.

Treatment of urinary incontinence can take a variety of forms. Most simply, the patient can wear absorptive devices or clothing, which is often sufficient for minor leakage events. Alternatively or additionally, patients may undertake exercises intended to strengthen the muscles in the pelvic region, or may attempt a behavior modification intended to reduce the incidence of urinary leakage.

In cases where such non-interventional approaches are inadequate or unacceptable, the patient may undergo surgery to correct the problem. A wide variety of procedures have been developed to correct urinary incontinence in women. Several of these procedures are specifically intended to support the bladder neck region. For example, sutures, straps or other artificial structures are often looped around the bladder neck and affixed to the pelvis, the endopelvic fascia, the ligaments which support the bladder, or the like. Other procedures involve surgical injections of bulking agents, inflatable balloons, or other elements to mechanically support the bladder neck.

In work done related to the present invention, it has been proposed to treat urinary incontinence by selectively remodeling a portion of the pelvic support tissue, often so as to reposition the bladder and/or urogenital tract. U.S. Pat. No. 6,091,995 generally describes laparoscopic and other minimally invasive devices, methods, and systems for shrinking tissues, particularly for treatment of incontinence. U.S. Pat. No. 6,216,704, describes noninvasive devices, methods, and systems for shrinking of tissues, often by cooling a surface of an intermediate tissue and directing energy through the cooled intermediate tissue to the target tissue so as to effect shrinkage. U.S. Pat. No. 6,156,060, is directed to static devices and methods to shrink tissues for incontinence. Finally, U.S. Pat. No. 6,292,700 describes an endopelvic fascia treatment for incontinence in which a strength of a collagenous tissue increases, optionally without collagenous tissue contraction. Each of these patents is assigned to the present assignee, and their full disclosures are incorporated herein by reference.

While these recent proposals for treatment of incontinence represent significant advancements in the art, treatment of incontinence and other conditions related to insufficient collagenous pelvic tissue support could benefit from still further advances.

BRIEF SUMMARY OF THE INVENTION

The present invention provides improved devices, systems, and method for treating incontinence. The invention will often heat volumes of collagenous support tissue such as the endopelvic fascia, the volumes typically being between about 100 and about 800 cubic millimeters. These volumes of tissues can be heated for sufficient time to effect substantial collagenous tissue shrinkage, for example, by heating the volume to a temperature of about 70° C. or more for about 30 seconds or more. Alternative treatments may heat the volume to about 65° C. or more for about 100 seconds or more, or to about 75° C. or more for about 10 seconds or more. Such heating may induce necrosis, but the heating will often be limited to inhibit ablation so that the tissue, after healing, provides continence promoting support. In some embodiments, a probe body may directly engage the endopelvic fascia, such as by introducing an endoscopic probe into the body adjacent the endopelvic fascia, or by surgically displacing a flap from the vaginal wall. Alternatively, the probe body may be separated from the endopelvic fascia, with heating provided through (for example) the vaginal wall. In either case, tissue-penetrating electrodes may be used to heat the endopelvic fascia.

In a first aspect, the invention provides a method for treating incontinence. The method comprises aligning a probe body with a collagenous pelvic tissue. A treatment volume of at least 100 cubic millimeters (often being at least 300 cubic millimeters) of the collagenous tissue is heated using the probe. The heating may optionally be performed so that the treatment volume is heated to a temperature of at least about 70° C. for a time of at least about 30 seconds. An intermediate tissue may (but need not) be disposed between the probe and target tissue, and/or heating may be effected using tissue-penetrating electrodes. Moreover, applying a dwell time after the desired heating temperature is achieved may also serve to increase treatment tissue volume as discussed in more detail below.

When an intermediate tissue is disposed between the probe body and the treatment volume, the treatment volume generally will be separated from the aligned probe body by a distance within a range of about 2 to about 8 mm, optionally being disposed throughout a range of at least 2 to about 4 mm from a vaginal wall surface engaged by the aligned probe. When the probe body directly accesses the treatment volume, treatment may extend to the probe body, for example, by using tissue-penetrating electrodes having active electrode surfaces that extend from the tissue-engaging surface by a distance within a range of about 0 to about 8 mm. The treatment volume will preferably be separated from a urethra of a patient by at least about 1 cm to inhibit injury to nerves along the urethra, with the treatment volume preferably being offset laterally from the urethra to a right side of the patient (for example). In such embodiments, the method may further comprise heating another treatment volume similarly offset laterally from the urethra to a left side of the patient. The treatment volume may have a length orientation extending proximally-distally along the urethra, a depth orientation extending between the collagenous tissue and the probe body, and a medial-lateral width orientation, the width of the treatment volume being greater than the length of the treatment volume, so that the treatment volume is elongated along the medial-lateral orientation of the patient. Alternatively, the length of the treatment volume may be greater than the width of the treatment volume in some embodiments.

The position of the treatment volume may be registered along an axis of the urethra with reference to a guide body disposed within the urethra. The treatment volume may, in some embodiments, be registered with reference to a bone of the patient, optionally with reference to a pelvic bone as can be identified with tactile examination through the vaginal wall, by a bone-receiving registration indentation of the probe, or the like.

Preferably, heating is performed so as to inhibit necrosis of any intermediate tissue, optionally while cooling the intermediate tissue. In other embodiments, heating may be performed without cooling of the intermediate tissue, for example, by advancing a plurality of tissue-penetrating electrodes from the probe body into the treatment volume and applying electrical potential to the tissue-penetrating electrodes. Electrically insulating a proximal portion of the tissue-penetrating electrodes from the intermediate tissue may inhibit necrosis of the intermediate tissue. Still further, heating may be performed by tip movement of at least a pair of electrodes supported by the probe body. In such an embodiment, the treatment volume may increase as the tip movement speed decreases.

In another aspect, the invention provides a system for treating incontinence of a patient having a collagenous pelvic tissue. The system comprises a probe body alignable with the collagenous pelvic tissue, optionally so that an intermediate tissue is disposed therebetween. At least one energy delivery element is supported by the probe body. The at least one energy delivery element is capable of heating, from the aligned probe body, a treatment volume of at least 100 cubic millimeters of the collagenous tissue to a temperature of at least 70° C. for a time of at least 30 seconds so that the collagenous pelvic tissue contributes to continence.

The system may further comprise at least one cooling element supported by the probe body so as to provide cooling of the intermediate tissue while heating the treatment volume. In such a cooled electrode embodiment, the at least one energy delivery element may comprise a plurality of electrodes. The electrodes may take on a variety of shapes, sizes, spacings, and numbers. In some cases the electrodes may have a width of at least 20 mm and a length of less than 8 mm. Alternatively, the at least one energy delivery element may simply comprise energizing a distal or proximal pair of electrodes on a probe body that carries a plurality of electrodes. Still further, the at least one energy delivery element may comprise a pair of elongated electrodes.

The at least one energy delivery element may also comprise an array of tissue-penetrating elements. The tissue-penetrating elements may similarly take on a variety of shapes, sizes, spacings, and numbers. For example, the tissue-penetrating element may comprise needle electrodes having diameters in a range from about 0.035 inch to about 0.125 inch. The tissue-penetrating elements may also comprise any one of blade electrodes, planar electrodes, C shaped electrodes, corkscrew shaped electrodes, or tissue-penetrating electrode tips. The tissue-penetrating elements may comprise an array from two to twenty tissue-penetrating electrodes, wherein such elements may extend from a tissue-engaging surface by a distance within a range from about 0 to about 8 mm. Still further, the tissue-penetrating elements may be formed from shape memory alloy or like deformable materials so as to be expandable.

Generally, that at least one energy delivery element heats the treatment volume of collagenous tissue by the application of bipolar radio frequency energy. However, it will be appreciated that alternative energy sources and/or monopolar operation may be utilized as well by any of the devices and methods described herein. Further, a guide body may be disposable within a urethra so as to register a position of the treatment volume along an axis of the urethra. Typically, the guide body comprises axial position indicators or electromagnetic transmitters as discussed in more detail below.

In a further aspect of the invention, another method for treating incontinence is provided. A probe body is aligned with a collagenous pelvic tissue. A plurality of tissue-penetrating electrodes as discussed above are advanced into the collagenous tissue from the aligned probe body. A treatment volume of at least 300 cubic millimeters of the collagenous tissue is heated using the aligned probe. The heating is performed so that the treatment volume is heated to a temperature of at least 70° C. for a time of at least 30 seconds.

In a still further aspect of the invention, another system for treating incontinence of a patient having a collagenous pelvic tissue is provided. The system comprises a probe body alignable with the collagenous pelvic tissue and a plurality of tissue-penetrating electrodes supported by the probe body. The electrodes are capable of heating, from the aligned probe body, a treatment volume of at least 300 cubic millimeters of the collagenous tissue to a temperature of at least 70° C. for a time of at least 30 seconds so that the collagenous pelvic tissue contributes to continence. Such a system may further incorporate at least one cooling element supported by the probe so as to provide cooling of the tissue while heating the treatment volume with the tissue-penetrating elements.

A further understanding of the nature and advantages of the present invention will become apparent by reference to the remaining portions of the specification and drawings.

BRIEF DESCRIPTION OF THE DRAWINGS

The following drawings should be read with reference to the detailed description. Like numbers in different drawings refer to like elements. The drawings, which are not necessarily to scale, illustratively depict embodiments of the present invention and are not intended to limit the scope of the invention.

FIGS. 6 and 6A illustrate non-invasive vaginal probes and a method for non-invasively treating endopelvic fascia using cooled electrodes.

FIGS. 7A-7I illustrate urethral guides to assist in registration of the treatment probe with a target volume of collagenous tissue.

FIG. 11 graphically illustrates maximum tissue temperatures of tissue heated using a non-invasive probe similar to that of FIGS. 6 and 6A.

FIGS. 21A-21C illustrate still further alternative tissue-penetrating electrode structures.

FIGS. 22A and 22B illustrate a tissue-penetrating electrode extending from a probe body having a cooled surface electrode.

FIG. 23 illustrates the development of treatment volume at a temperature of above 70° C. as a function of dwell time.

DETAILED DESCRIPTION OF THE INVENTION

The present invention generally provides methods, devices, and systems which enhance the structural support provided by a body's tissues, particularly for treatment of incontinence. The techniques of the invention generally involve directing energy from a probe into collagenous tissues of the pelvic support system. The energy will often cause contraction of the collagenous tissue. In some embodiments, the formation of scar tissue and/or the healing process may cause structural stiffening of the tissue.

As the techniques of the present invention will be effective for controllably and repeatably enhancing the structural support of a wide variety of fascia and other collagenous tissues throughout the body, they will find applications in a wide variety of therapies. The most immediate application of the invention will be to enhance a tissue system's support of the urethra and bladder neck so as to contribute to urinary continence, often without having to resort to sutures, slings, fasteners, or other artificial support structures. In many embodiments, these treatments will be performed so as to inhibit ablation of the target collagenous tissues. As used herein, the term "ablation" of a tissue means that the tissue is substantially removed and/or the function of the tissue is substantially destroyed. Hence, although tissue necrosis may occur, and while the structural strength of a tissue may initially decrease immediately after treatment, the treated tissue will generally continue to provide at least some structural support and the structural strength will often increase during the healing process.

Figure 1:
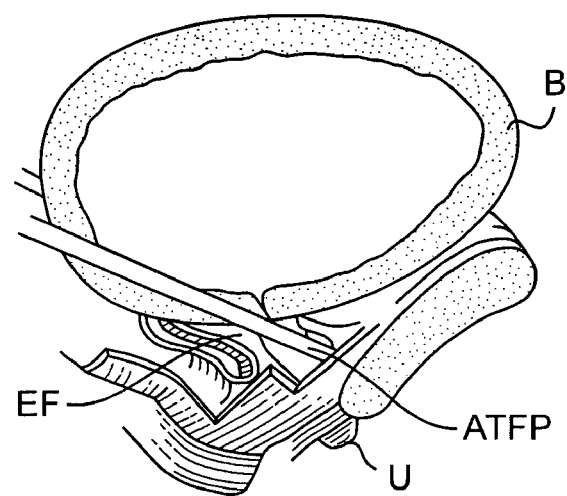
FIG. 1 illustrates pelvic support tissues which may be targeted for treatment using the system and methods of the present invention.

The tissues of the pelvic support system generally maintain the position of the genitourinary tract, and particularly the position of urinary bladder B, urethra U, and the bladder neck coupling these structures as illustrated in FIG. 1. In general, endopelvic fascia EF may define a hammock-like structure which extends laterally between the left and right arcus tendineus fasciae pelvis (ATFP). These tendon structures may extend substantially between the anterior and posterior portions of the pelvis, so that the endopelvic fascia EF at least partially defines the pelvic floor.

The fascial tissue of the pelvic floor may comprise tissues referred to under different names by surgeons of different disciplines, and possibly even by different practitioners within a specialty. In fact, some surgeons may assign a collagenous support structure of the endopelvic fascia one name when viewed from a superior approach, and a different name when viewed from an inferior approach. Some of the endopelvic fascia may comprise two collagenous layers with a thin muscular layer therebetween, or may comprise a single collagenous layer. The hammock-like endopelvic fascia described herein may be damaged or missing, particularly after pregnancy, so that the support of the genitourinary tract is instead provided by a variety of fascial layers, muscular tissues, ligaments, and/or tendons within the pelvis. Hence, the treatment of the present invention may be directed at a variety of tissue structures defining the pelvic floor and/or diaphragm (including: anterior sacrococcygeal ligament; arcus tendineus fasciae pelvis ATFP, the white line of the pelvis; fasciae of the obturator internus muscle; the arcus tendineus levator ani or "picket fence" to the iliococcygeus portion of the levator ani muscle; bulbocavernosus muscle; ischiocavemosus muscle; urethrovaginal sphincter; m. compressor urethrae muscle; and m. sphincter urethrovaginal muscle which replaces deep perineal muscle); structures of the bladder and urethra (including: urethrovesical fascia; detrusor muscle; and the pubo-coccygeus muscle which relaxes to open the bladder neck, initiating micturation); structures of the vagina (including: vagino-uterine fascia, lamina propria—the dense connective tissue layer just under the epithelium; pubourethral or puboprostatic ligaments; pubo-vesicle ligament and posterior pubo-urethral or puboprostatic ligament; pubovesicle muscle, a smooth muscle that is integrated with the pubovesicle ligament; and pubocervical fascia which attaches to the ATFP); structures of the uterus (including: round ligament; sacrouterine ligament; and broad ligament); and structures of the bowel (including: rectal fascia and mackenrodt's ligament).

When the endopelvic fascia has excessive length or stretches excessively under a load, the fluid pressure within the bladder advances into the bladder neck and down the urethra more readily. Leakage may result in part because the endopelvic fascia allows the bladder, bladder neck, and/or urethra to drop below its desired position, at which fluid pressure within the bladder may actually help to seal the bladder neck. Stretching of the endopelvic fascia may also alter the timing of pressure pulse transmission to the urethra.

When a continent woman coughs, the pressure in the urethra will often increase more than one-tenth of a second prior to the increase in bladder pressure. In women with stress incontinence, the bladder pressure may rise first. For a continent woman having endopelvic fascia which stretches much less under the influence of a pressure pulse, the time delay between initiation of the pressure pulse and transferring sufficient force to urethra U to effect closure may therefore be significantly less. By treating the endopelvic fascia to decrease its length and/or increase its stiffness, the descent time of the pelvic viscera during a cough will be shorter than an untreated, excessively long and/or excessively elastic tissue.

Figure 2:
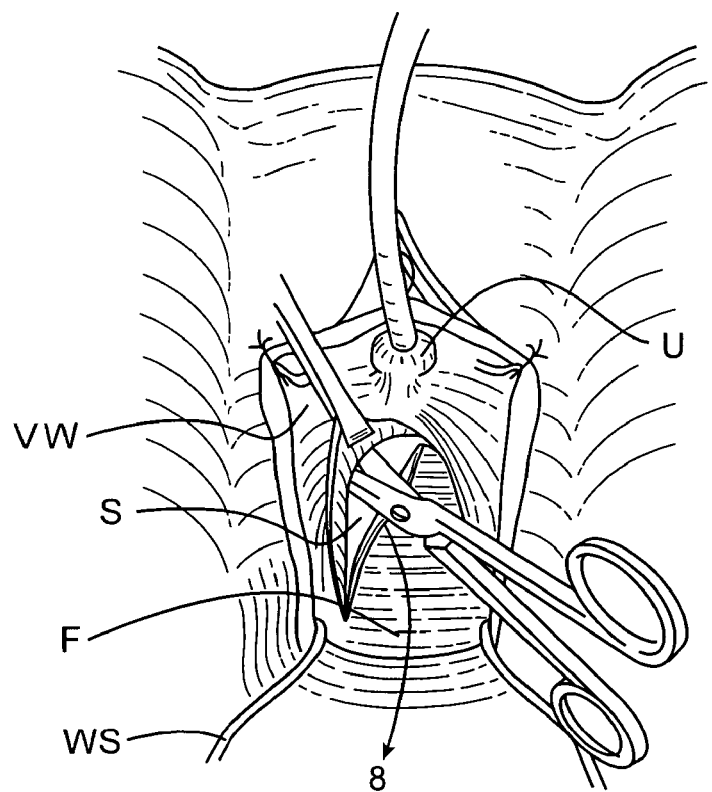
FIG. 2 illustrates a method for accessing endopelvic fascia for direct treatment.

Referring now to FIG. 2, the endopelvic fascia may be treated non-surgically or it may be accessed for direct treatment in a variety of ways. FIG. 2 illustrates one method for accessing surface S of endopelvic fascia EF transvaginally, by forming and displacing a flap F from the vaginal wall VW with the assistance of a weighted speculum WS as depicted by arrow 8.

Figure 3A:
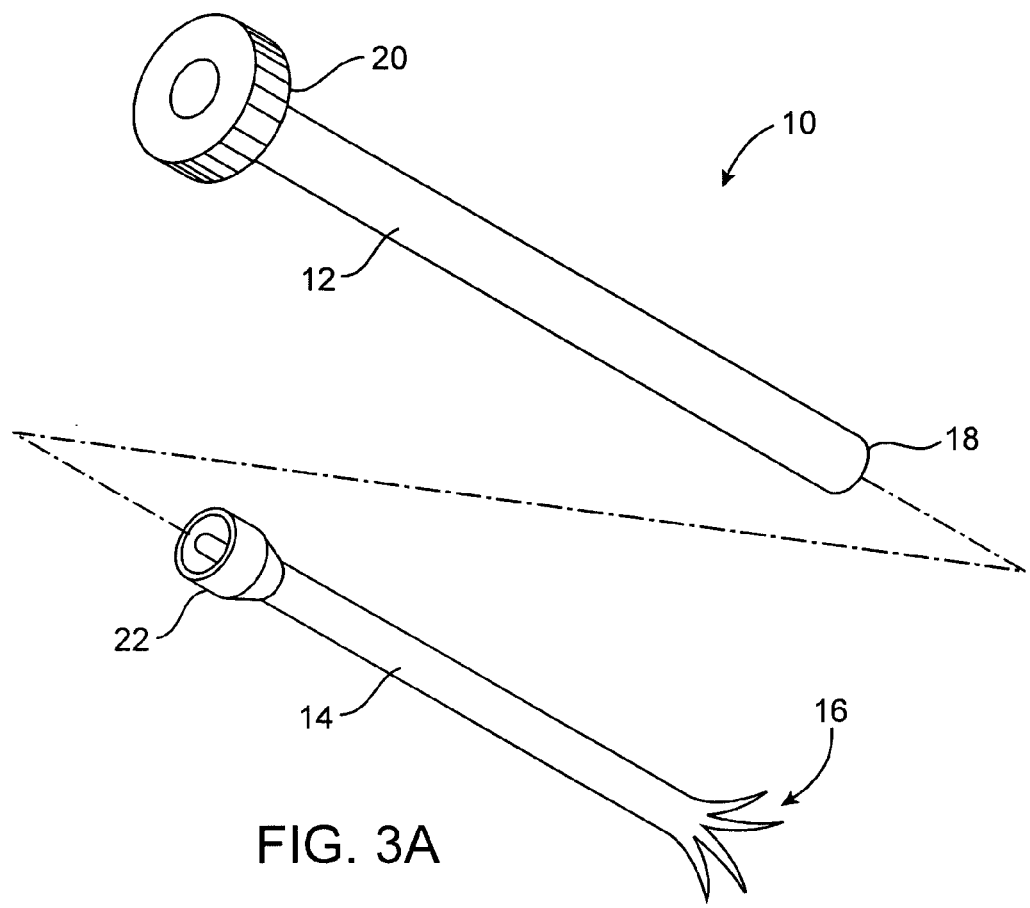
FIGS. 3A-3C illustrate a probe having tissue-penetrating electrodes for treatment of incontinence.
Figure 3B:
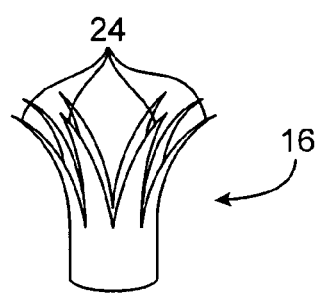
Figure 3C:
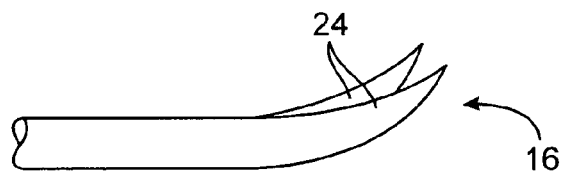

Referring now to FIGS. 3A-3C, a heat applying probe 10 comprises a probe body having a sheath component 12 and an electrical rod component 14. The electrode rod 14 is reciprocately mounted in a lumen of sheath 12 so that a distal electrode array 16 on the rod 14 may be retracted and extended into and from the distal end 18 of sheath 12. A proximal handle 20 is provided on the sheath, and a proximal connector 22 is provided on the electrode rod component 14. Electrode array 16, as illustrated, may optionally include four individual tissue-penetrating electrode tips 24, with each tip having a sharpened distal end suitable for penetrating into tissue, particularly for transmucosal penetration through the vaginal wall and into the tissue structures which support the urethra, urinary sphincter, bladder neck, and the like. In other embodiments, between two and twenty tissue-penetrating electrodes might be used as shown in FIG. 3B. It will be appreciated that the above depictions are for illustrative purposes only and do not necessarily reflect the actual shape, size, or dimensions of the probe 10. This applies to all depictions hereinafter.

Electrode tips 24 are sufficiently resilient so they will be radially contracted when rod 14 is withdrawn proximally into sheath 18. Electrode tips 24 will resiliently expand from the sheath when the electrode rod component 14 is advanced distally after sheath 18 is positioned near the target site, as discussed in more detail below. As illustrated, electrode tips 24 are commonly connected to a single plug in connector 22. Thus, probe 10 may be suitable for monopolar operation. Multiple electrode tips 24 may alternatively be connected through separate, isolated conductors within rod 14 and further be connected through multiple pins in connector 22. Thus, probe 10 could be readily adapted for bipolar operation. Usually, all components of the probe will be insulated other than the electrode tips 24. Alternatively, some other portion of rod 14 or sheath 12 could be formed from an electrically conductive material and utilized as a common or indifferent electrode so that the probe could be utilized in a bipolar manner. In still further alternatives, multiple insulated and conductive areas may be used, with the specific configuration optionally depending on the relationship of the electrodes to the probe itself, so that more than one return electrode might be employed. A variety of such modifications would be possible with the basic probe design.

Figure 4A:
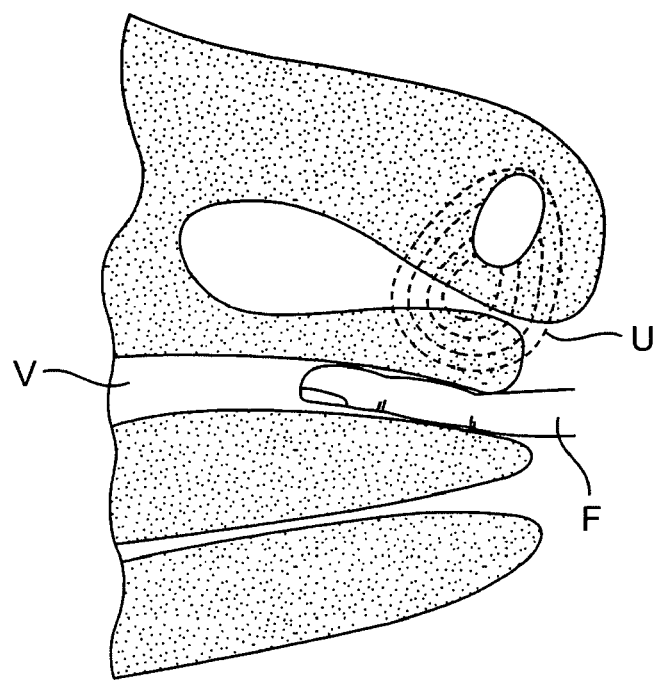
FIGS. 4A-4D illustrate a method for using the probe of FIGS. 3A-3C for treatment of incontinence.
Figure 4B:
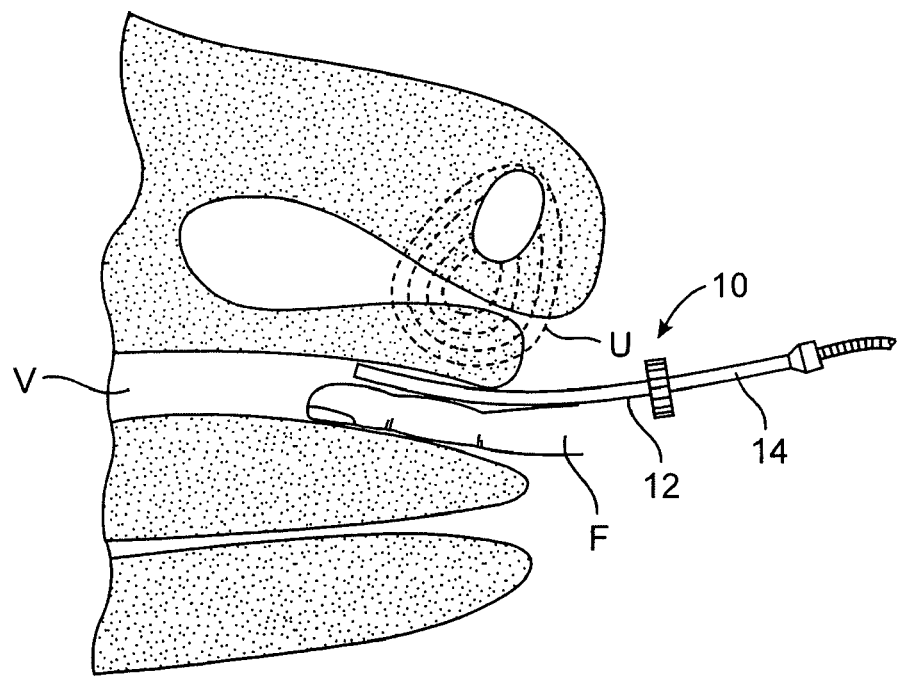

Referring now to FIGS. 4A-4D, use of probe 10 for contracting tissue ligaments, fascia, and other collagenous tissues which support the urethra and/or bladder neck will be described. Initially, the treating physician manually examines the vagina V to locate the region within the vagina adjacent the target region of the endopelvic fascia. Probe 10 is then introduced into the vagina as shown by FIG. 4B. Conveniently, the physician may manually locate the probe, again by feeling the region of the endopelvic fascia which is to be targeted for treatment. Specifically, the physician may identify the treatment region as a portion of the endopelvic fascia laterally offset (to the patient's right or left) from the urethra, ideally with the treatment region being separated from the urethra by at least one centimeter. Identifying the location of the urethra may be facilitated by the use of a guide body extending into or through the urethra, as described in co-pending U.S. patent application Ser. No. 10/301,561, filed Nov. 20, 2002, and entitled Incontinence Treatment with Urethral Guide, the full disclosure of which is incorporated herein by reference. Positioning of the target region along the axis of the urethra may be facilitated by identifying the axial position of pubic bone PB using finger F and/or by an axial location indicator of the urethral guide. Preferably, the location of the treatment volume of endopelvic fascia will be disposed along a length of the urethra between the bladder neck and the external meatus so as to avoid injuring nerves (which might otherwise have deleterious impacts on urge incontinence and the like) while still enhancing the structural support sufficiently to inhibit leakage.

Figure 4C:
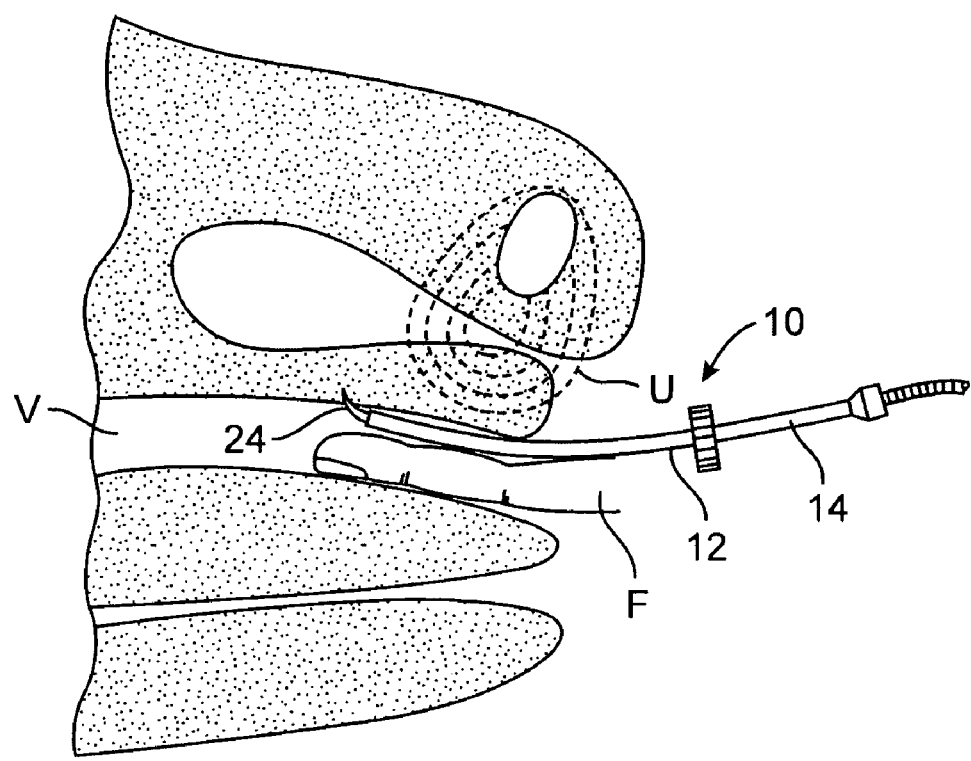
Figure 4D:
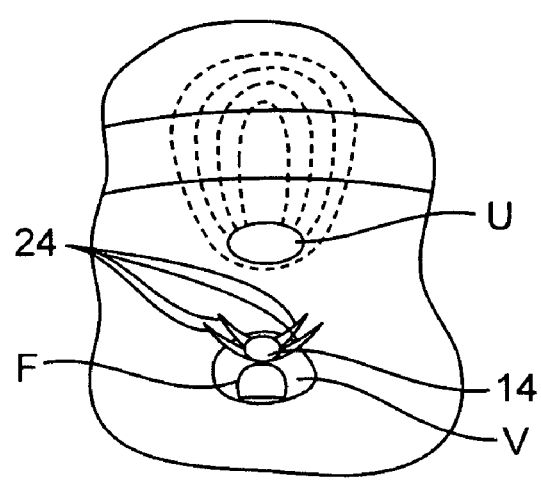

After sheath 12 of probe 10 is properly positioned, the rod component 14 will be distally advanced so that electrode tips 24 penetrate into the tissue which supports the urethra as shown in FIG. 4C. The physician will continue to use a finger F to hold the probe against the vaginal wall to facilitate penetration of the electrode tips 24. RF energy can then be applied through the probe in order to heat the target tissue to temperatures and for time periods which effect a contraction of the collagen within the target tissue and/or enhance stiffening of the support provided by these structures. The supporting collagenous tissues, immediately and/or upon healing, thereby contribute to continence.

Figure 5A:
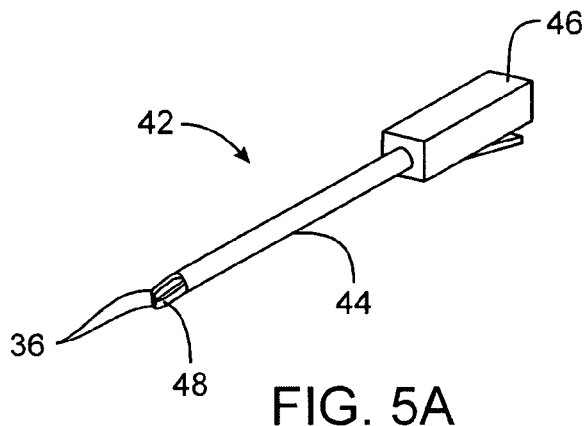
FIGS. 5A and 5B illustrate probes and methods for treating incontinence by surgically accessing endopelvic fascia.
Figure 5B:
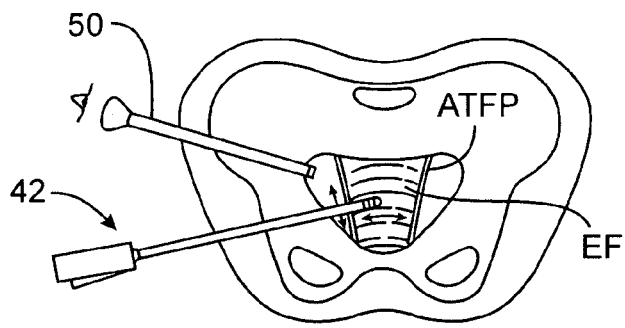

Referring now to FIG. 5A, a direct probe 42 may be suitable for laparoscopic use and/or use through a transvaginal incision. With reference to FIGS. 5A and 5B, a method for using direct probe 42 for directly heating endopelvic fascia EF via a laparoscopic approach can be understood. Direct probe 42 includes a shaft 44 supporting an electrode pair 36 relative to handle 46. A variety of electrode pair configurations might be used, as more fully described in co-pending U.S. patent application Ser. No. 08/910,370, the disclosure of which is also incorporated by reference. Preferably, a port 48 will be disposed adjacent and/or between electrodes 36 to allow a small amount of irrigation flow before and/or during the treatment. The irrigation flow may comprise a conductive fluid such as saline or a non-conductive fluid, and will ideally be sufficient to avoid accumulation of residue on the electrode pair surfaces. Suitable flow rates will often be in range from about 0.5 cc/min to about 2.0 cc/min.

Direct probe 42 may optionally be used in a laparoscope procedure using a superior approach, typically under the direction of a laparoscope 50 inserted near the patient's mid-line (for example, adjacent the belly button). Handle 46 is manipulated so as to "paint" bipolar electrode 36 across the endopelvic fascia surface until the target region has been sufficiently heated. Alternative surgical methods for use of related probes may access the endopelvic fascia using an inferior approach, preferably with a small transvaginal incision as illustrated in FIG. 2.

Figure 6:
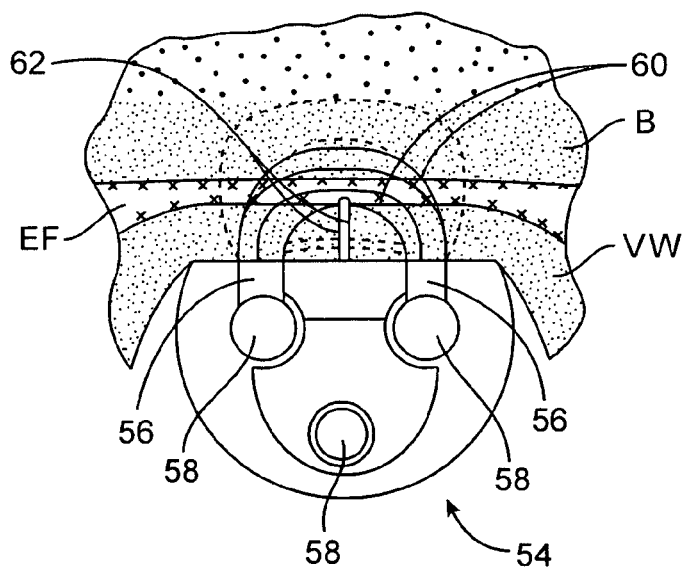

FIGS. 6 and 6A illustrate alternative cooled electrode vaginal probes for indirect treatment of tissue to inhibit incontinence through an intervening or intermediate tissue, which may comprise a spared zone or safety zone where tissue necrosis is inhibited. In these embodiments, a vaginal probe body 54 includes a plurality of electrodes 56 which are cooled by fluid conduits 58. The fluid conduits cool the intervening or intermediate tissue between probe body 54 and the endopelvic fascia EF, such as the vaginal wall VW as seen in FIG. 6. The probe body between electrodes 56 also cools the intervening tissue. Once the intervening tissue of the vaginal wall VW (and optionally, the urethra, bladder neck, and bladder) are cooled sufficiently, RF current is transmitted between the electrodes of the probe body to heat the endopelvic fascia. Advantageously, the pre-cooling can inhibit heating of the intervening tissue to a temperature causing surface lesions within the vagina. Feedback on the pre-cooling and heating temperatures may be provided by needle-mounted temperature sensors 62 which may optionally be reciprocately advancable from probe body 54 through a sensor port 64. A relatively flat tissue-engaging electrode surface helps direct electrical current flux 60 toward the endopelvic fascia, while electrically insulating film disposed over at least a portion of electrodes 56 near an adjacent electrode may inhibit edge-induced flux concentration. Exemplary cooled electrode structures are described in more detail in U.S. Pat. No. 6,283,987 entitled Ribbed Electrodes and Methods for Their Use, the full disclosure of which is incorporated herein by reference. As can be understood by comparison of FIGS. 6 and 6A, the electrodes may extend axially along a length of the probe body, or may each have a conductive surface which is elongated in the lateral orientation, with probe bodies having more than two electrodes preferably utilizing bipolar RF energy between alternating pairs of the electrodes.

FIGS. 7A-7I schematically illustrate alternative urethral guides to assist in registration of the probe treatment body relative to a target tissue. Urethral guides 70a, 70b, 70c, and 70d (collectively, urethral guides 70) may generally assist in tactile location of the urethral axis so as to facilitate separating the treatment zone laterally from the urethra. Urethral guides 70 may also include axial position indicators to help locate the treatment zone along the urethral axis. For example, urethral guide 70a includes a distal balloon 72 for identifying an axial position of the bladder or bladder neck, and a proximal positioning surface 74 for engaging the external meatus EM of the patient. A first elongate body of urethral guide 70a is axially coupled to balloon 72, and a second body 76 of guide 70a is coupled to positioning surface 74. A position indicator 78 of the body 76 facilitates reading an indicia of position from the first elongate body, allowing the overall length between bladder B and the external meatus EM to be readily identified. This facilitates identification of the midpoint of the urethra, urinary sphincter, and the like. The urethral guide body may include a balloon-fill lumen, a bladder draining lumen, temperature and/or pressure sensors, transmitter cables, and the like.

Referring to FIGS. 7B-7C, once the axial position of the centroid or sphincter for the urethra is identified, it may be possible to generate a palpatory marker for axial registration of the treatment zone as shown. Specifically, a radially distensible urethral guide tube 80 may house first and second actuation rods 82, 84, with the second rod here being in the form of a tube in which the first rod is disposed. Distal bodies at the distal ends of the first and second actuation rods 82, 84 expand the distendable tube when aligned as illustrated in FIG. 7C. Expanded portion 86 may be identified by finger F of the physician through the vaginal wall.

More sophisticated axial and/or lateral registration systems may be included in the urethral guide and/or treatment probe as schematically illustrated in FIG. 7D. In this embodiment, distal and proximal electromagnetic transmitters or coils 71, 73 may be sensed by sensors or receivers 75 of the treatment probe, or vice versa. For example, a plurality of transmitters 71, 73 are positioned on the urethral guide 70c within the patient body and four Hall effect sensors 75 are positioned on the right and left sides of the treatment probe tip 77. By individually triangulating distances between the transmitters 71, 73 and sensors 75 using the Hall effect, the relative lateral and axial positioning of the treatment probe and urethra may be identified. In particular, the information from the Hall effect sensors 75 may be transmitted to amplifiers and subject to signal processing, as depicted by block 67, for information display, as depicted by block 69. Alternatively, as the sensors can be much smaller than the transmitters, the sensors may be supported by the urethral guide while the transmitters are supported by the vaginal probe. These structures may be more fully understood with reference to U.S. patent application Ser. No. 10/301,561, previously incorporated herein by reference.

Figure 7A:
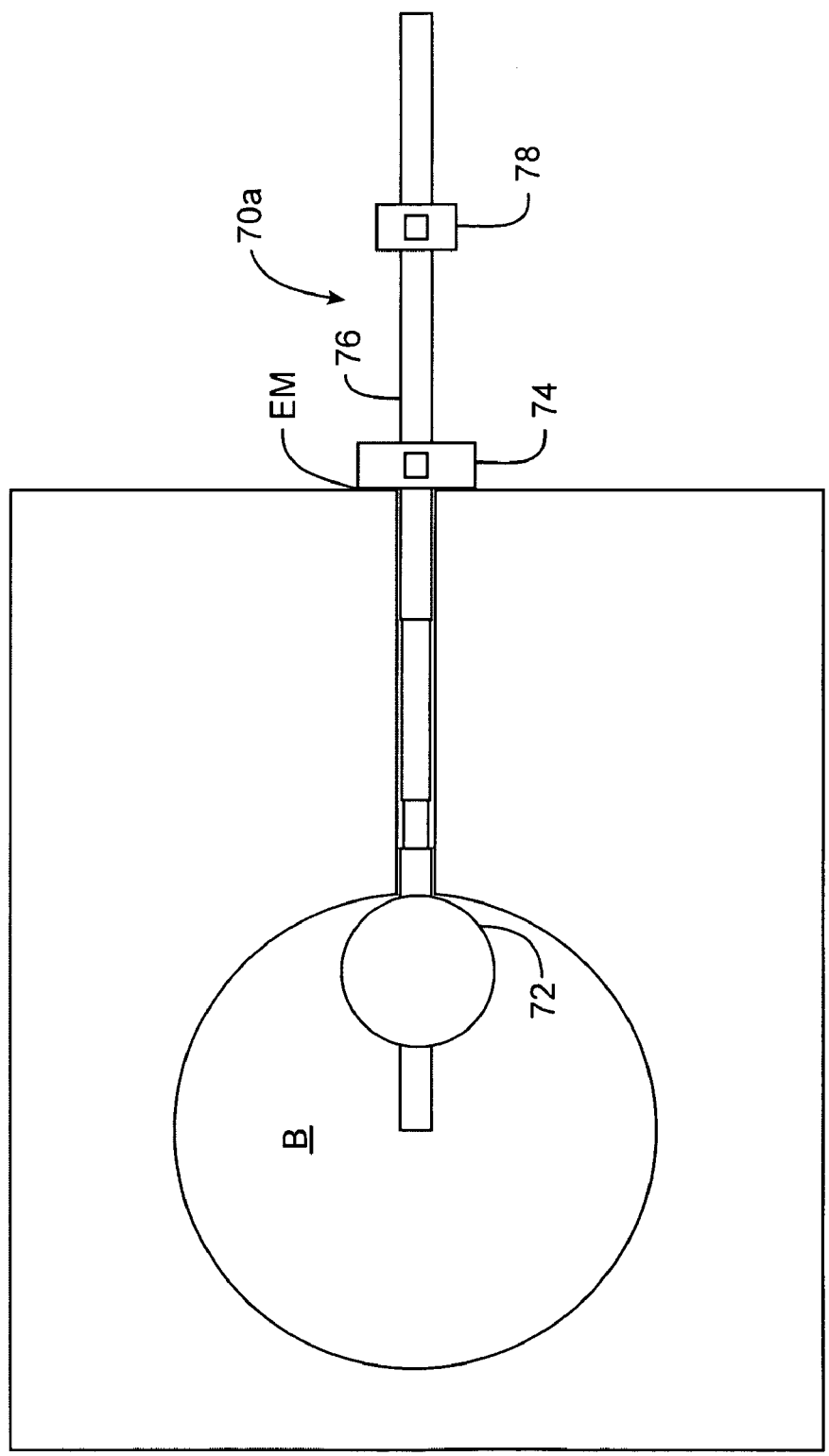
Figures 7E, 7F:
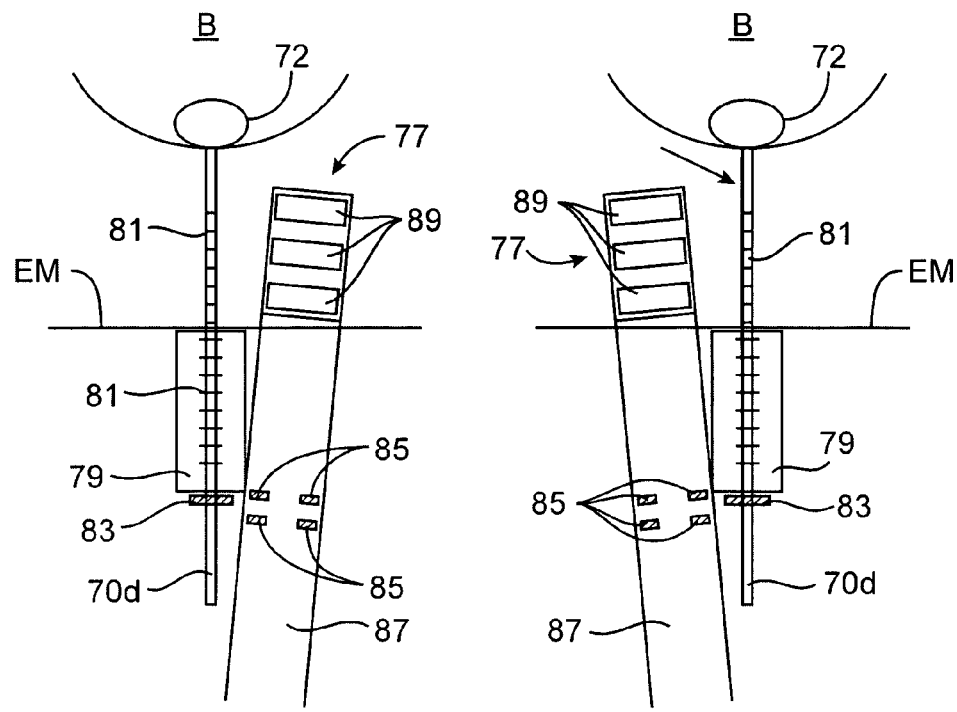

Still more complex urethral guide measurement mechanisms may also be provided, including those having separately moveable threaded bodies for positioning of transmitters, sensors, and the like. FIGS. 7E-7I illustrate such an embodiment. The urethral guide 70d and adjustable magnetic assembly 79 are provided with a series of measurement graduations 81. The urethral guide 70d is inserted, the bladder B is drained, the balloon 72 is inflated, and the urethral guide 70d and balloon 72 are pulled proximally to contact the bladder neck, as illustrated in FIGS. 7E and 7F. The magnetic assembly 79 is initially pulled in a proximal direction so it is not in contact with the external meatus EM. The graduation 81 on the urethral guide 70d closest to the external meatus EM is then read to provide the urethral length. The magnetic assembly 79 is then advanced distally until the separate set of graduations 81 on the magnetic assembly 79 match the measured urethral length reading. This mechanism includes adjusting screws with thread ratios such that advancing the magnetic assembly 79 to this graduation will place the electromagnetic transmitter or coil 83 in the desired position. The Hall effect sensors or receivers 85 mounted in the probe handle 87 will bracket the single disk or doughnut shaped magnet 83, as shown in FIGS. 7E and 7F. This bracketing allows for the treatment zone to be centered approximately around the middle of the urethra for heating by electrodes 89 on the probe tip 77. In this embodiment, lateral positioning may be achieved by palpation of the urethral guide 70d by using a finger of the F of the physician.

Figure 7G:
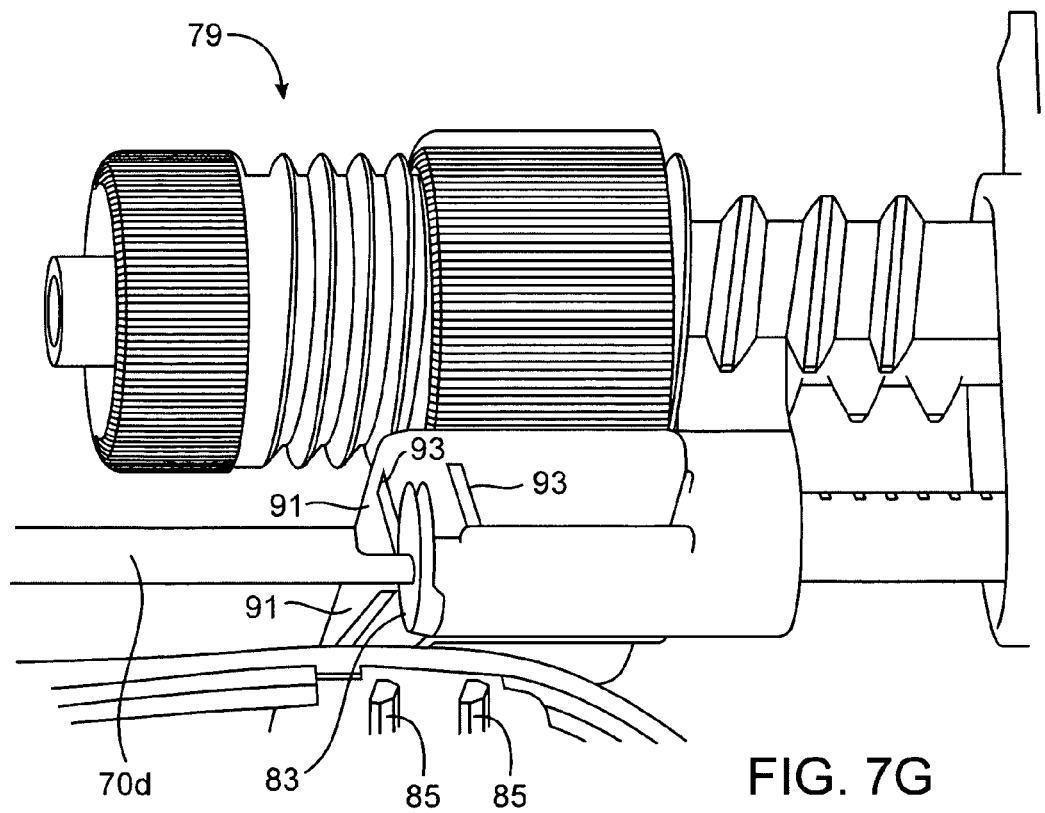
Figure 7H:
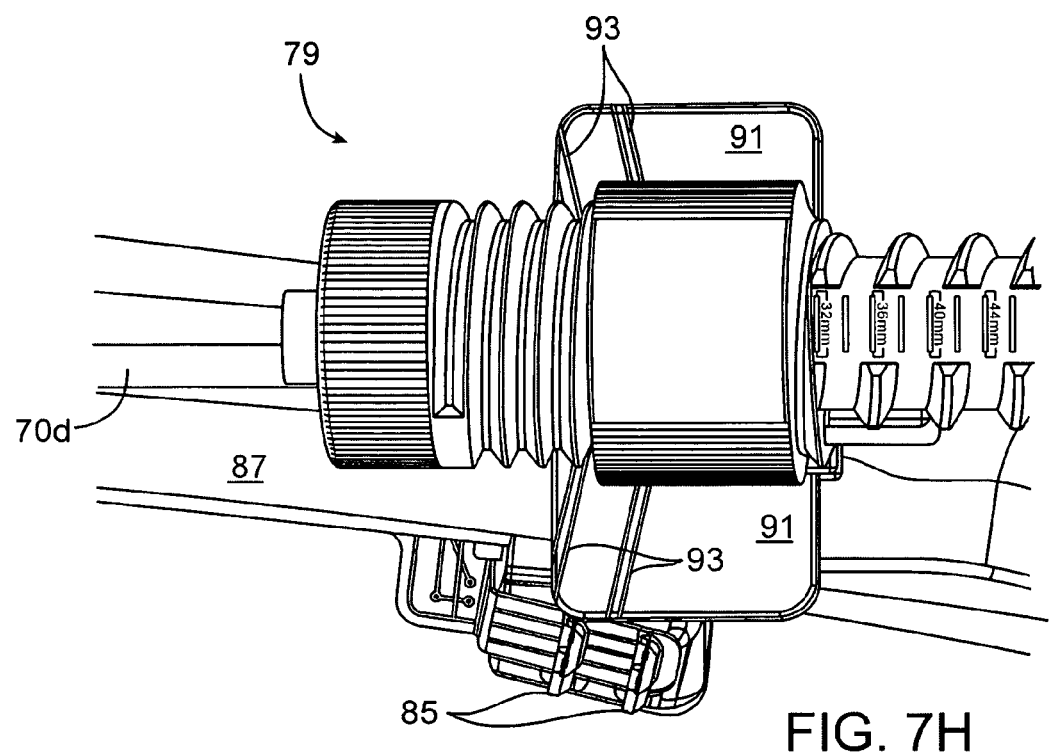
Figure 7I:
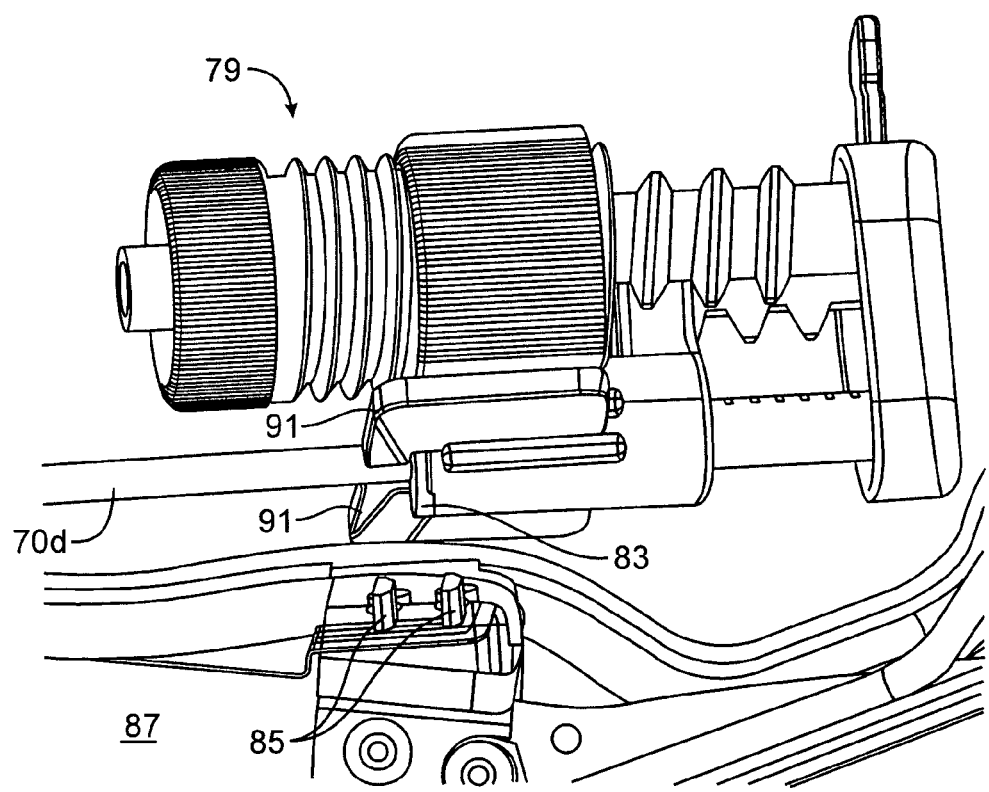

FIG. 7E illustrates treatment of a patient's left side by positioning two Hall effect sensors 85 on the left side of the probe handle 87. FIG. 7F illustrates treatment of a patient's right side with positioning of two Hall effect sensors 85 on the right side of the probe handle 87. FIGS. 7G-7I illustrate exploded views of the adjustable magnetic holder 79 and electromagnetic transmitter 83 around the urethral guide 70d and outside the patient body. Such placement of the electromagnetic transmitter 83 provides several advantages. For example, the size of the electromagnetic transmitter 83 is no longer constrained by the size of the urethral guide as it is positioned outside the body. As such, a larger electromagnetic transmitter 83 may in turn be utilized to allow for enhanced signal detection. Moreover, placement of the electromagnetic transmitter 83 outside the patient body further allows for a smaller urethral guide profile which in turn adds to patient comfort and allows for more complete bladder draining. As best seen in FIGS. 7H and 7I, a V shaped transparent plastic flap, flange, or pointer 91 may be coupled to the electromagnetic transmitter 83 so that a physician may visually align the probe 87, 77 with the urethral guide 70d. In particular, a pair of lines 93 on the flap 91 center the electromagnetic transmitter 83 and may be visually aligned with the two Hall effect sensors 85 on the probe handle 87 by approximately ¼ of an inch or less correct positioning. Moreover, the flap 91 also provides both distal and proximal positioning into the patient body.

Figures 8A, 8B:
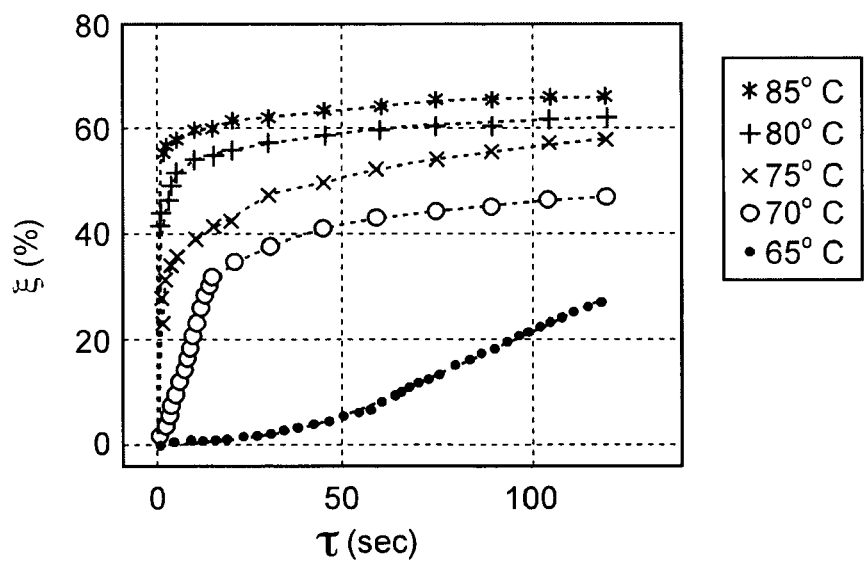
FIGS. 8A and 8B illustrate shrinkage and necrosis effects of heating on tissue.

Referring now to FIGS. 8A-8B, effects of heating on collagenous tissues are shown. As can be understood with reference to FIG. 8A, to obtain a significant percentage of shrinkage in a relatively short treatment time, it is generally advantageous to heat tissues to temperatures of about 70° C. or more. As can be understood with reference to FIG. 8B, heating tissues to temperatures of even 65° C. would result in necrosis in a short time period. Hence, by comparing FIGS. 8A and 8B, it will be understood that to effect significant heat-induced shrinkage, both the heated tissue and adjoining tissues will exhibit at least some necrosis. Once again, even though necrosis does occur, the collagenous tissue will not necessarily be "ablated" as it will remain at the treatment site and the collagenous tissue will retain its structural support function.

Necrosis will extend beyond the tissue undergoing shrinkage due to the diffusion of heat. As the necrosis sensitivity of the tissue is significantly more dependent on the temperature than on the time for which it is heated, it may be advantageous to (as practicable) limit treatment temperatures toward the lower possible temperatures from which sufficient tissue shrinkage can be provided. While this may require a treatment time of at least 10 seconds, preferably of at least 20 seconds, and typically of at least about 30 seconds, the size of the tissue region subjected to necrosis-inducing temperatures will often be less than if higher treatment temperatures are used. Hence, to effect significant, repeatable tissue shrinkage, it is generally desirable to subject the treatment volume to temperatures of at least 70° C. for a time of about 30 seconds or more.

Figure 9:
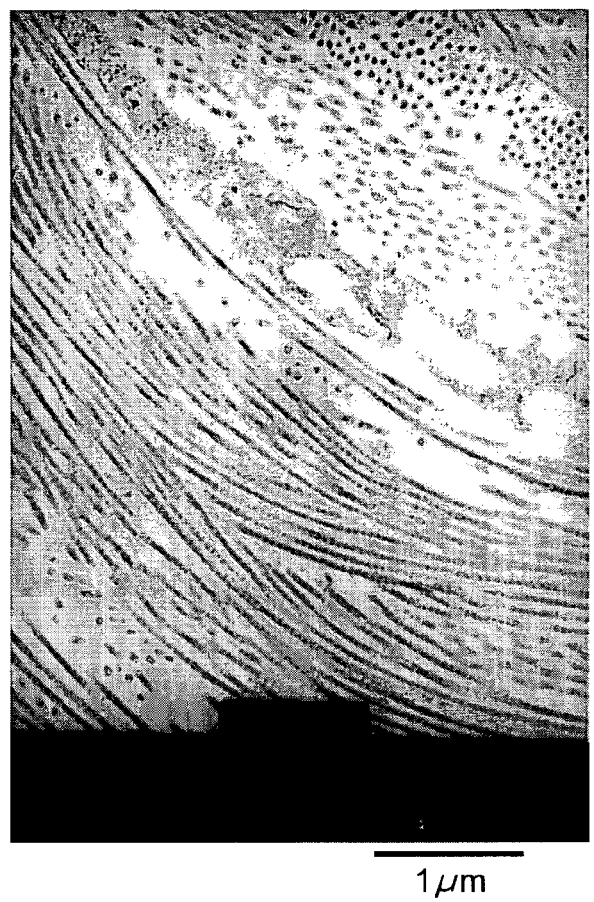
FIG. 9 illustrates a target collagenous tissue structure.

FIG. 9 illustrates the 2-D orientation of collagen fibers in the deep fascia, a preferred target tissue for incontinence treatments. The structure of tissues between a vaginal treatment probe and this deep fascia collagen of the endopelvic fascia includes typically about 0.04 mm of epithelium along the surface of the vaginal wall. Below the epithelium is between 0.04 mm and 0.7 mm of submucosa, typically comprising loosely packed thin collagen fibers. Below the submucosa lies a layer of superficial fascia, at a depth of between 0.7 mm to about 2.0 mm. This superficial fascia contains much smaller collagen bundles which are loosely packed and appear interlacing. The deep fascia illustrated in FIG. 9 typically lies throughout a depth of between about 2.0 and 4.0 mm, and includes larger, elongated collagen bundles having a distinct horizontal or 2-D distribution. This deep fascia provides an exemplary target for greater heat-induced changes, including contraction or shrinkage, stiffening, and/ or the like. RF heating will typically induce collagen shrinkage so as to provide physical elevation of the urethra by shrinkage of the endopelvic fascia. RF heating may also decrease the compliance of the endopelvic fascia to intra-abdominal pressures, providing increased stiffness through tissue remodeling resulting from the healing process. Within the first 24 hours of the heating treatment, fibroblasts will move in to begin repair. Over about two weeks, type III collagen will replace the denatured collagen, initially providing only a decreased tissue stiffness or low tensile strength. Within 8-12 weeks, the percentage of type I collagen will increase relative to the amount of type III collagen resulting in a return to about 85% of the original stiffness.

Figure 10A:
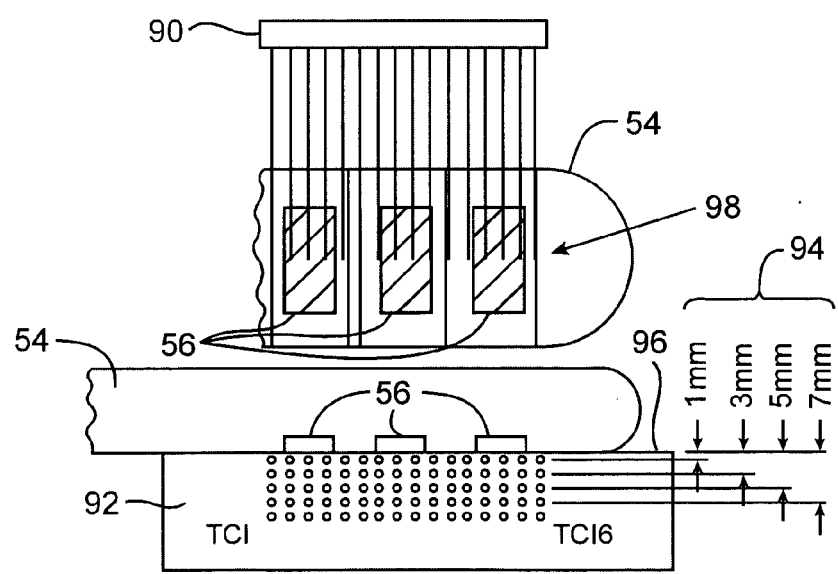
FIGS. 10A-10C illustrate in vitro and in vivo treatment temperature studies and the temperatures resulting from use of a non-invasive treatment probe similar to that of FIGS. 6 and 6A.
Figure 10B:
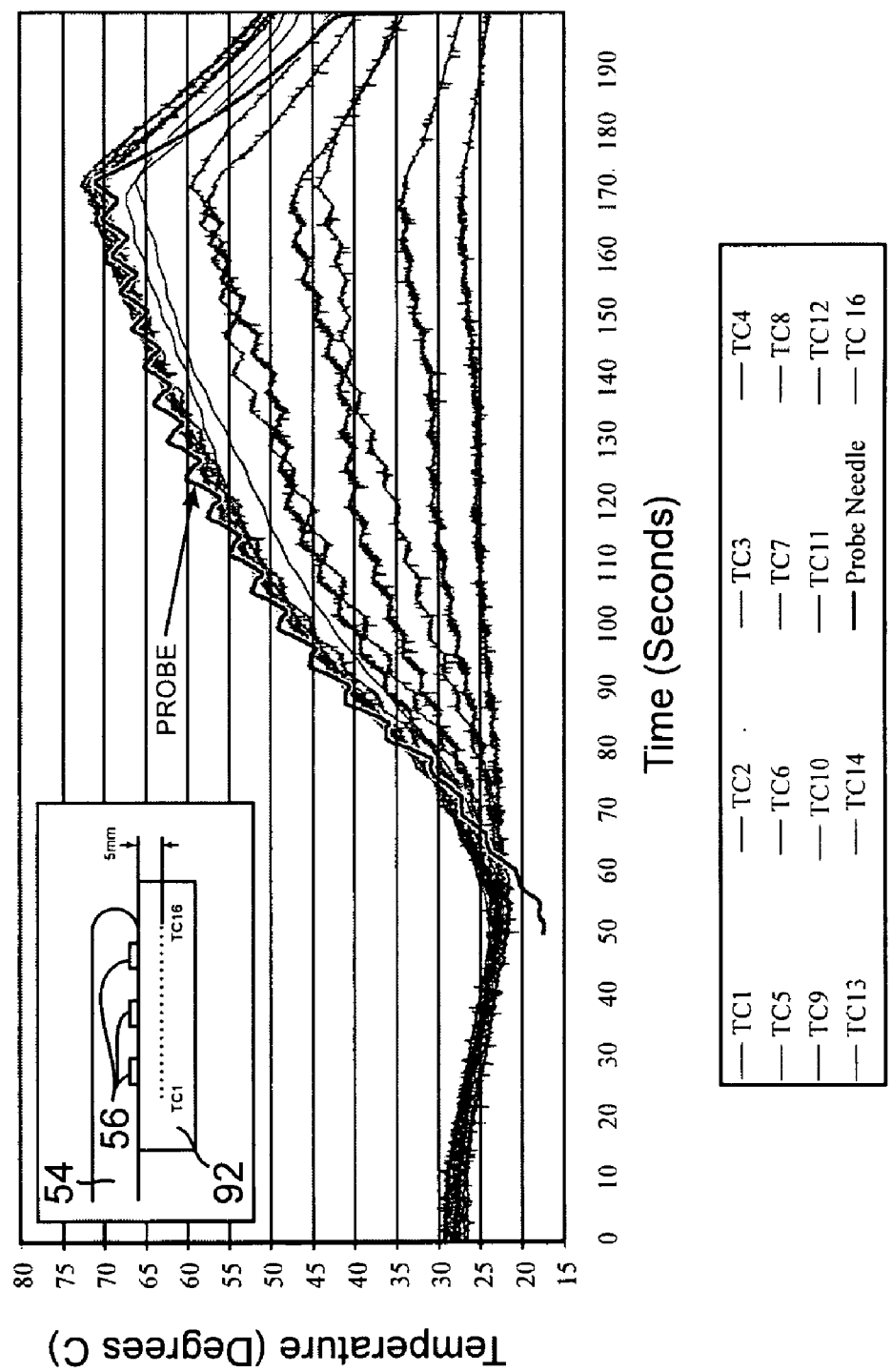
Figure 10C:
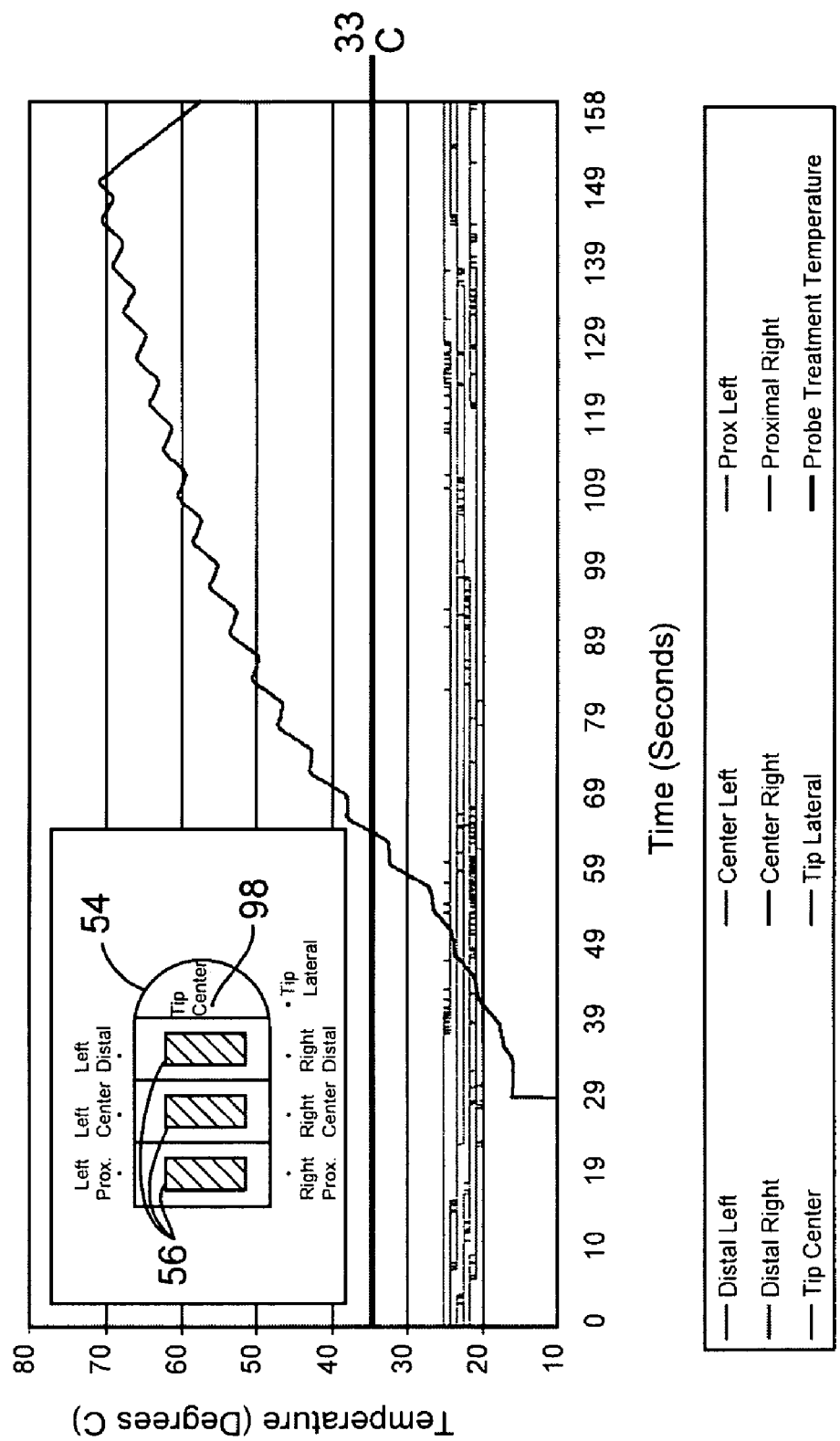

Referring now to FIGS. 10A-10C, a temperature study was performed to determine actual treatment temperatures induced by a non-invasive treatment probe 54 similar to that shown in FIGS. 6 and 6A. A linear array of sensing needles 90 was advanced into a model tissue 92 at a series of different depths 94 from a treatment surface 96. Each of the needles of array 90 carried a temperature sensor 98 (TC1 ... TC16), such as a thermocouple or the like, near the distal end of the needle. The needles were advanced at the selected depth from surface 96, and the probe 54 was aligned with electrodes 56 in engagement with tissue surface 96 such that the temperature sensors 98 were distributed along the center line of the probe and electrodes. This allowed a measurement profile of the tissue temperature to be taken at the selected depth along the treatment volume centerline.

The temperatures for the electrodes with the needles disposed at a depth of 5 mm are provided in FIG. 10B. The probe needle temperature indicated in FIG. 10B was taken by a probe-supported temperature sensor 62, as illustrated and described above with reference to FIGS. 6 and 6A. This needle was used in a feedback loop to control the RF energy applied by the probe, as explained in application Ser. No. 10/102596, filed on Mar. 19, 2002 and incorporated herein by reference. The sensing needles were then removed and inserted in a new tissue sample at the next depth 94, allowing a full profile of the tissue temperature along the target volume center line to be taken from a series of such tests.

In vitro and in vivo treatment temperatures were also taken with needle-supported thermocouples 98 inserted to locations offset laterally and/or axially from the electrodes 56, as illustrated in FIG. 10C. A comparison of in vitro tests and in vivo (from animal studies) temperatures indicated that in vitro temperature rise is slightly higher than in living tissue, and provides a good model which may be used as an upper bound for in vivo temperature results. The offset temperature sensors illustrated in FIG. 10C were positioned at depths 94 of 4 and 10 mm. Probe 54 makes use of cooling prior to and during RF energy application, and all measurement locations were maintained at or below standard tissue temperatures at the offset locations. Hence, these studies indicate there is no tissue heating beyond the footprint of probe 54, and lateral heat dispersion can be well controlled for the non-invasive application of RF energy using a cooled electrode non-invasive applicator.

Referring now to FIG. 11, the temperature profile along the center line of a non-invasive, cooled electrode vaginal probe is graphically illustrated at varying depths from the probe/tissue interface. While potentially effective for some patients, the quantity of tissue heated above 70° C. is somewhat limited, being about 12 cubic millimeters in this study. This volume was a result of a treatment method which ends heating as soon as tissue temperature reached 70° C. This limited treatment volume nonetheless provided a cured/ improved effectiveness rate, at six months after treatment, of over 50%.

Figure 12D:
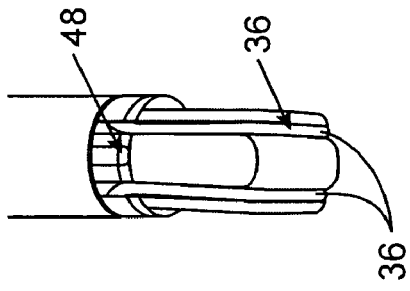
FIGS. 12A-12D illustrate tissue heating studies using a surgical probe similar to that of FIGS. 5A and 5B.
Figure 12C:
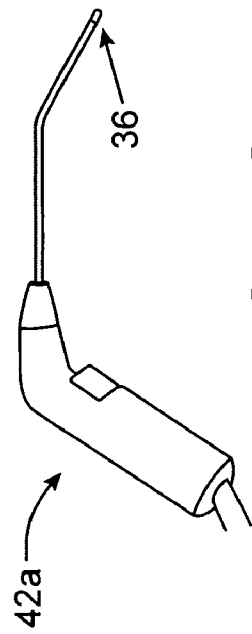
Figure 12A:
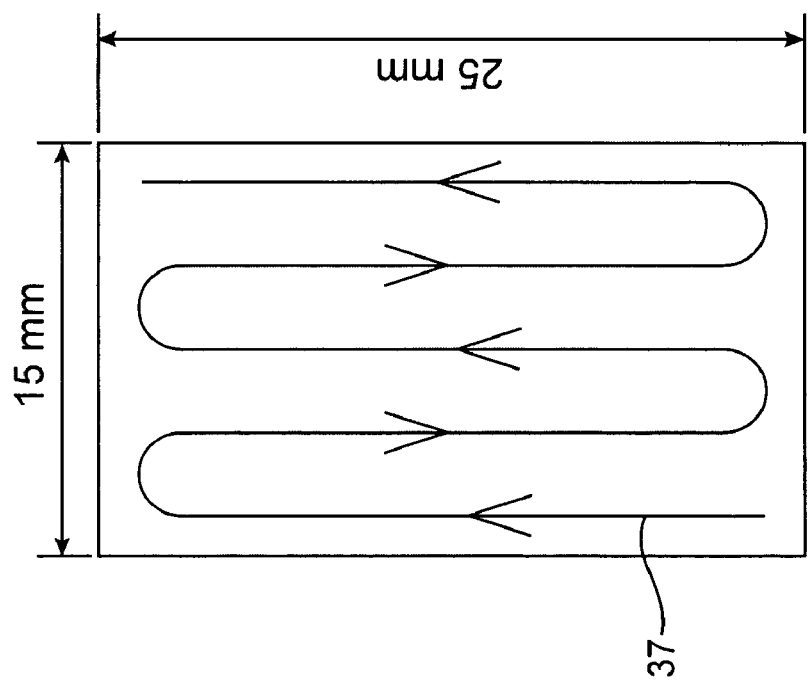
Figure 12B:
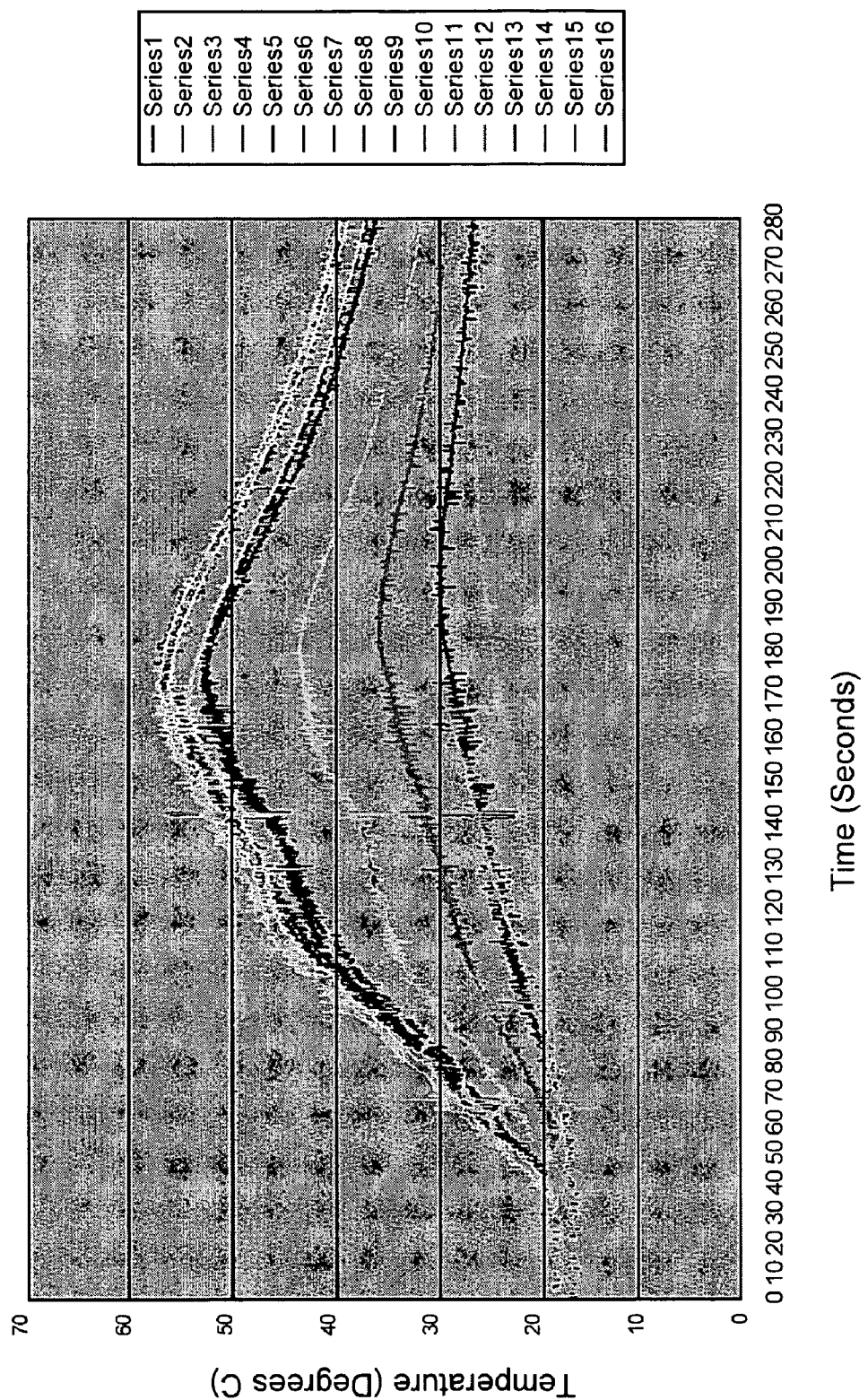
Figure 13A:
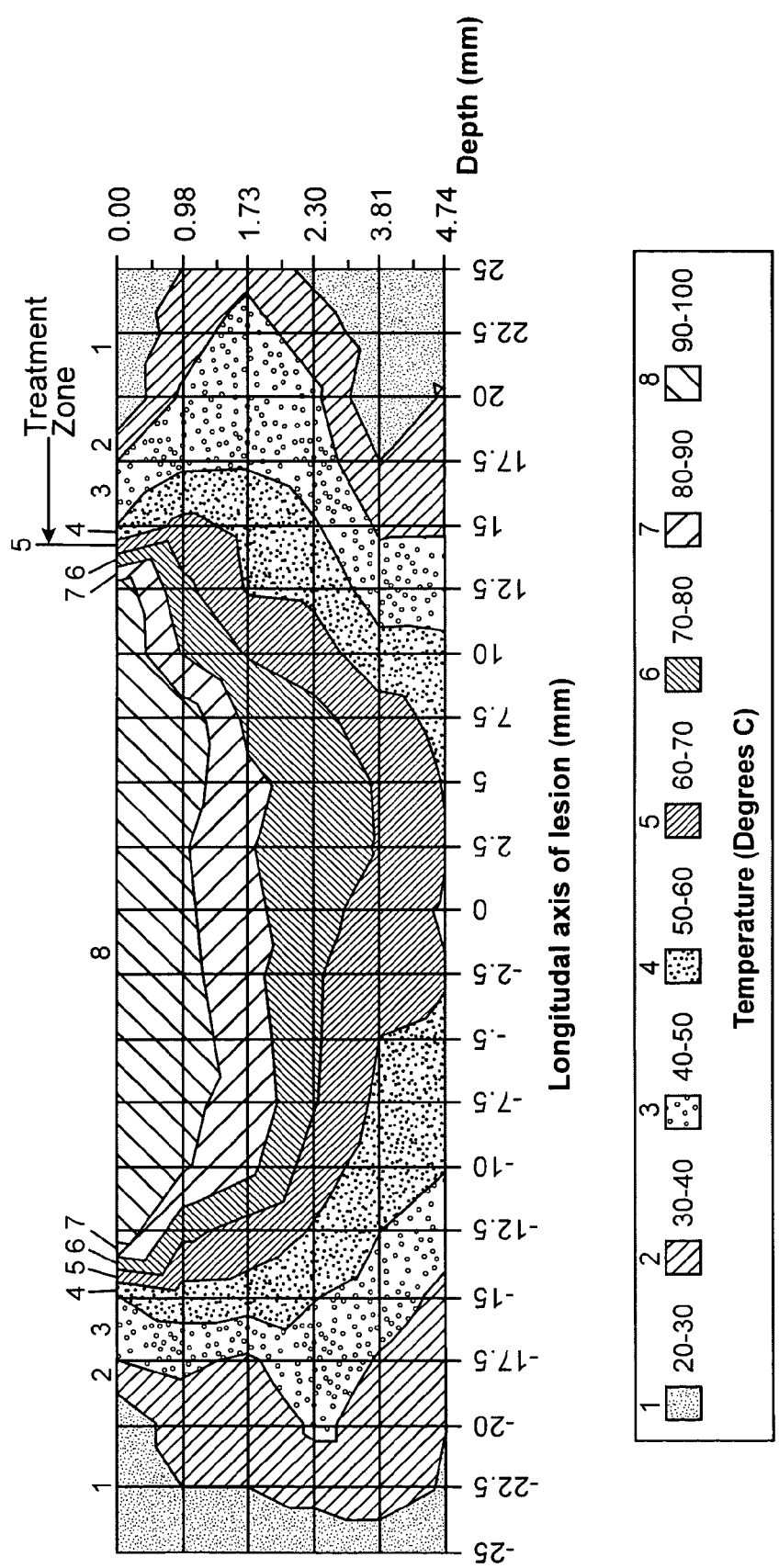
FIGS. 13A and 13B graphically illustrate tissue temperatures of tissue heated with a surgical probe per the studies of FIGS. 12A-12B.
Figure 13B:
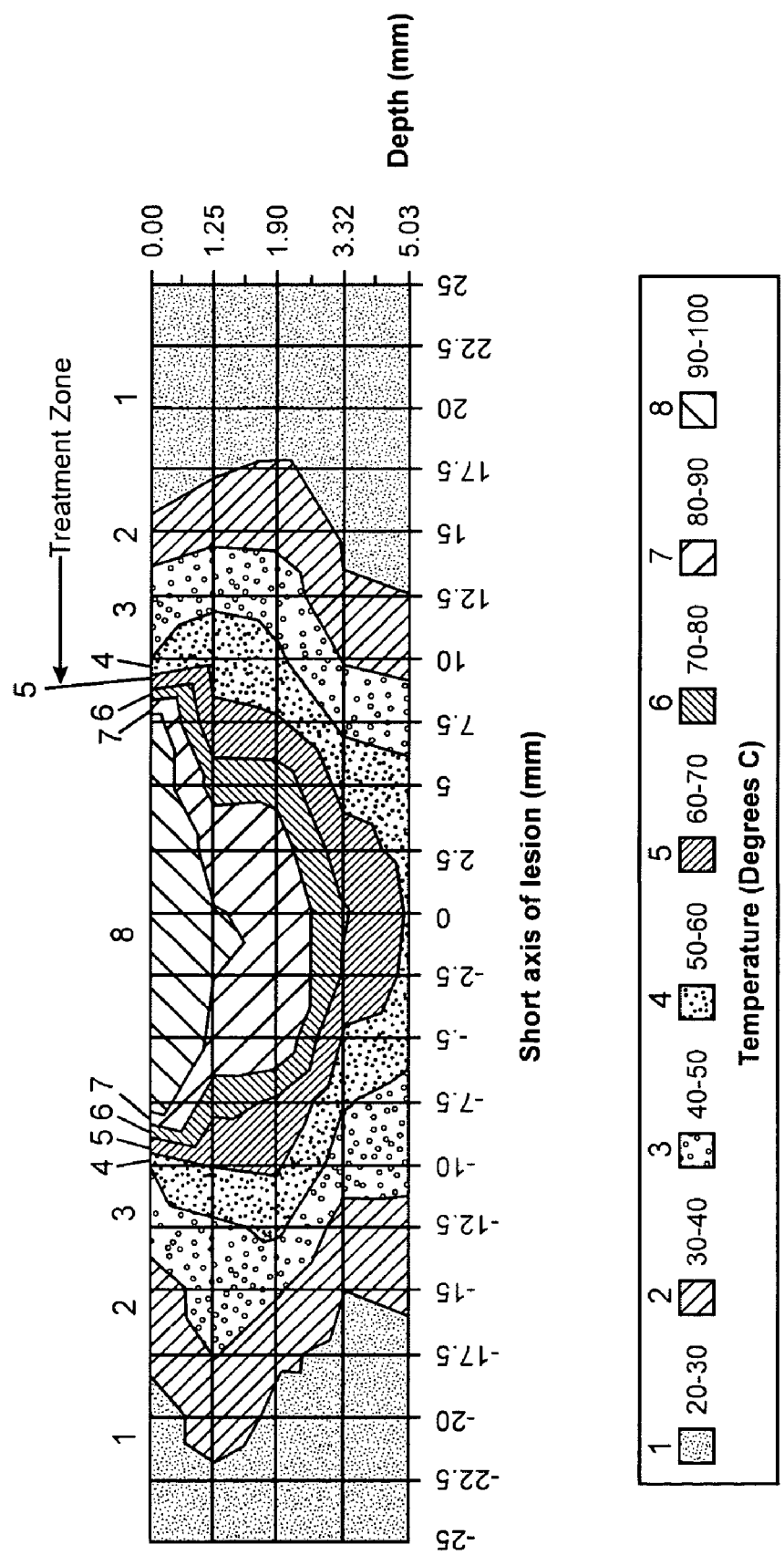
Figure 14:
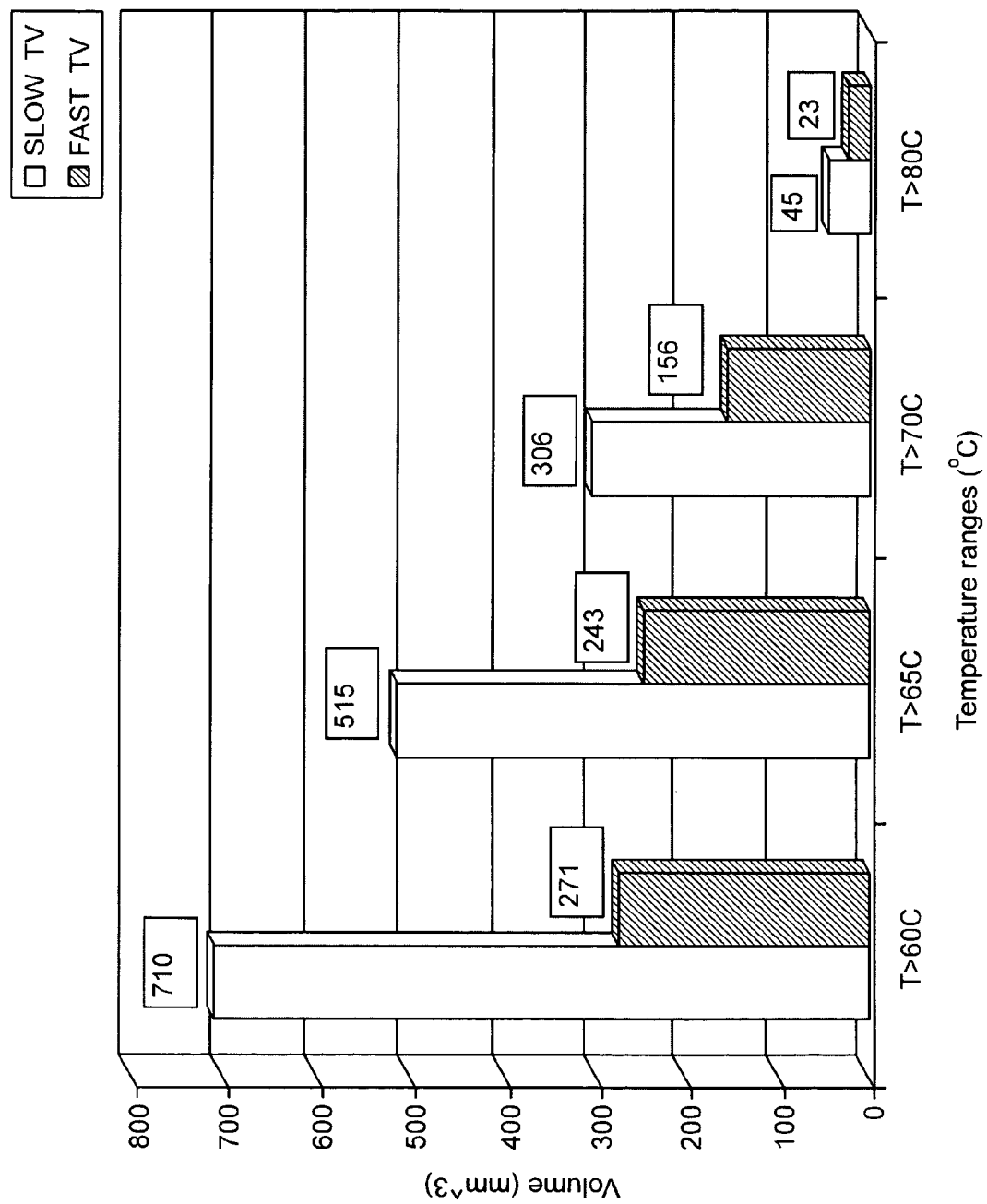
FIG. 14 illustrates treatment volumes of a tissue heated to various temperatures using surgical probes.

Referring now to FIG. 12B, additional tissue heating studies were performed using a surgical direct contact probe 42A, as shown in FIGS. 12C and 12D, similar to that described above regarding FIGS. 5A and B. Probe 42a was used to heat a treatment surface with a "paint" tip movement pattern as shown in FIG. 12A, using tip movement speeds of about 0.4 cm/sec. for a treatment of 140 seconds and tip movement speeds of about 1.1 cm/sec. for a treatment period of 90 seconds. Arrow 37 indicates a tip movement pattern of five passes in the treatment zone. Using a temperature sensor needle array similar to that shown above in FIG. 10A, treatment temperatures at different depths were measured along and beyond the longitudinal and width or short axis of the treatment region, with the temperature results being graphically illustrated in FIGS. 13A and 13B. The resultant treatment volumes for different temperatures are illustrated in FIG. 14, showing that the total treatment volume heated to 70° C. or greater was over 300 cubic millimeters when the slower tip movement was used, and about 150 cubic millimeters when the faster tip movement speeds were applied for a treatment time of 30 seconds.

Direct contact treatments were performed on patients suffering from urinary stress incontinence using laparoscopic and transvaginal approaches, as described above. The treatments generally involved direct access and treatment of the endopelvic fascia to both the right and left of the urethra using the treatments described above with reference to FIGS. 12A-13B. For these tests, about 75 to 80% or more of the patients were cured and/or improved as compared to prior to the treatments.

Figure 15:
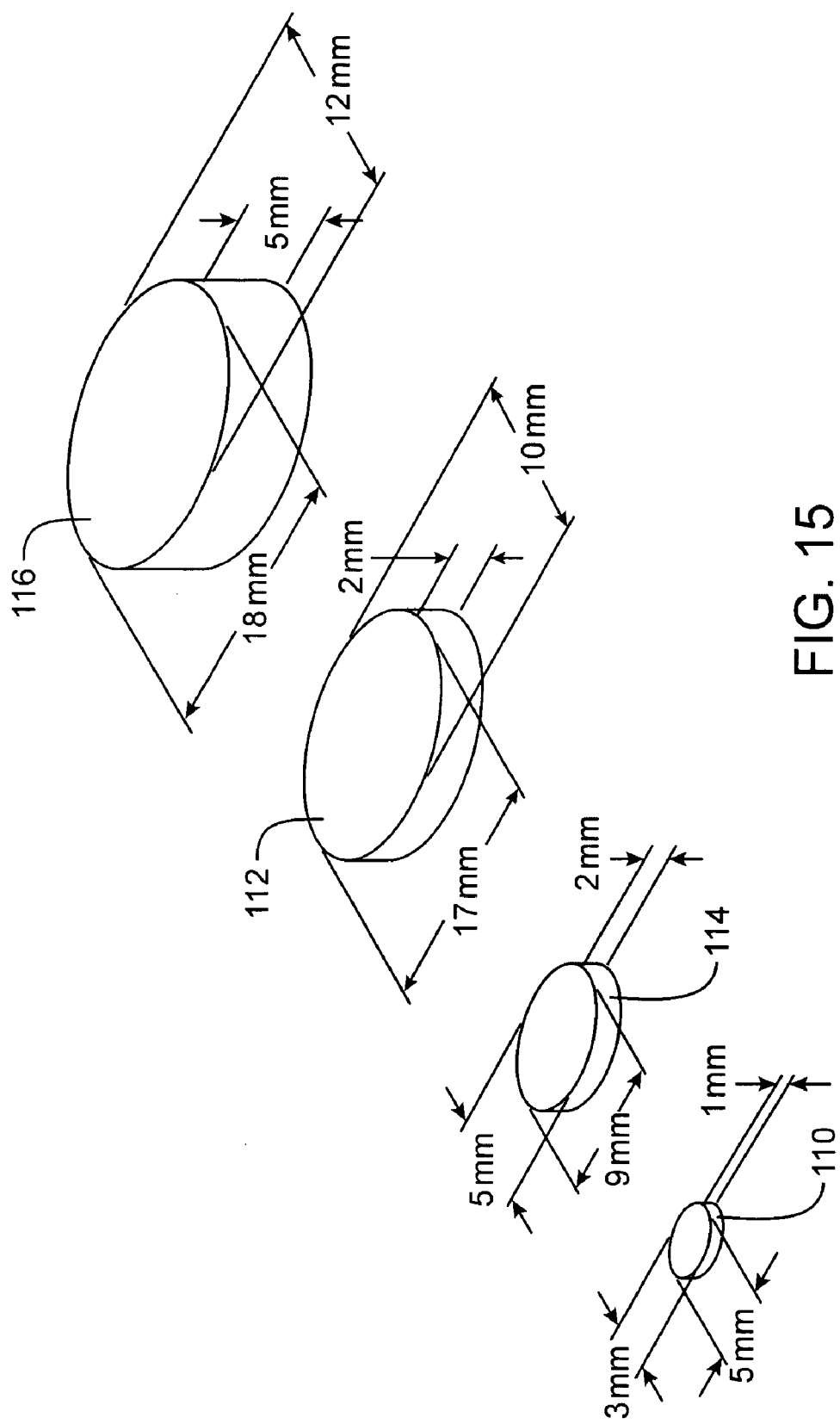
FIG. 15 graphically illustrates the different volumes of the tissues which can be heated to 70° with different probes and/or different treatment settings.

Referring now to FIG. 15, a graphic comparison of the treatment volumes for the cooled-electrode vaginal probe treatments and transvaginal direct access treatments are shown, along with rough dimensions of the treatment volumes in millimeters. Treatment volume 110 graphically illustrates the volume of tissue that will be heated above 70° C. per the non-invasive treatment probe study described in FIGS. 10A-11, while direct treatment volume 112 illustrates the volume of tissue that will be heated above 70° C. when the tissue is accessed using the transvaginal approach of FIG. 2. Treatment volume 114 illustrates the volume of tissue which will be heated above 70° C. when a similar non-invasive treatment is applied, but for a greater time with the treatment temperature maintained using the feedback loop from the probe-supported temperature sensing needle. Enhanced non-invasive volume 116 illustrates the volume of tissue which may be treated using the treatment probe from the studies of FIGS. 10A-11 when the treatment probe feedback temperature is increased to 85° C., and the treatment is maintained at that temperature for over 240 seconds. The total volume of tissue treated to temperatures above 70° C. for a time of greater than 30 seconds in effecting enhanced treatment volume 116 is over 900 cubic millimeters, so that non-invasive probes 54 are capable of treating sufficient endopelvic fascia to provide efficacy. Once again, each of the treatment volumes illustrated in FIG. 15 would often be applied on a first side of the patient's endopelvic fascia, with a similar treatment volume disposed on the opposed side of the endopelvic fascia relative to the urethra.

To avoid injury to nerves in the bladder neck region while providing sufficient treatment volume along the endopelvic fascia, it may be advantageous to distribute the treatment volume along the patient's lateral orientation while limiting the length of treatment along the axis of the patient's urethra. This may minimize exposure of the bladder neck and antero-lateral vaginal wall nerves to RF energy. Such a laterally elongated treatment region of the endopelvic fascia will preferably be significantly wider (along the medial-lateral orientation) than its urethral length, ideally having a width of about 25 mm and a length of about 15 mm. Treatment depths will preferably be at least about 2 mm, optionally being as much as 6 mm.

Figure 16A:
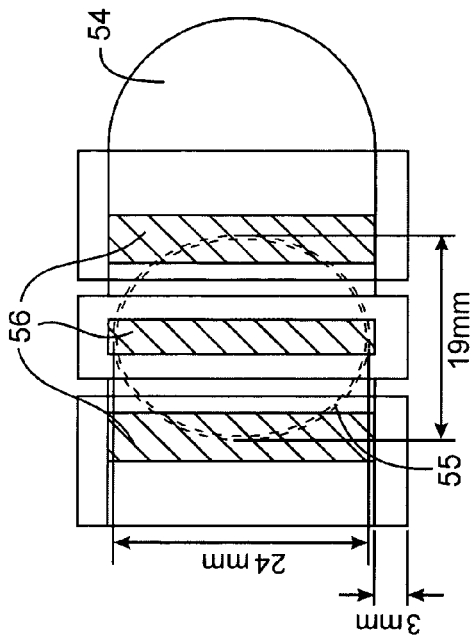
FIGS. 16A-16D illustrate a variety of cooled electrode configurations for vaginal probes and associated treatment regions produced thereby.
Figure 16B:
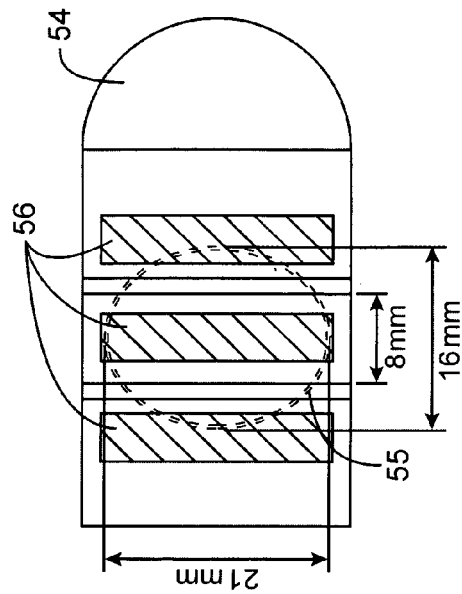
Figure 16C:
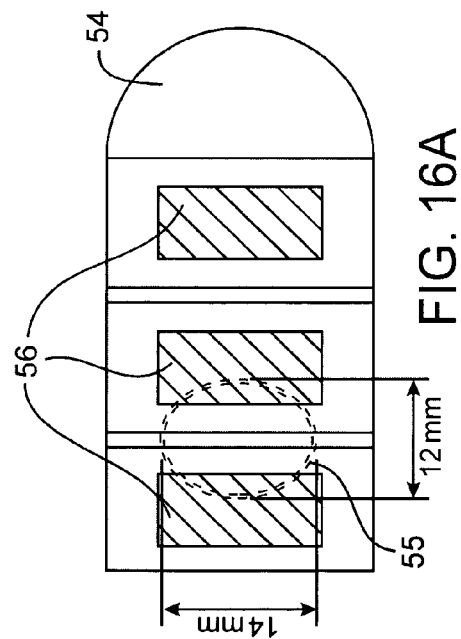
Figure 16D:
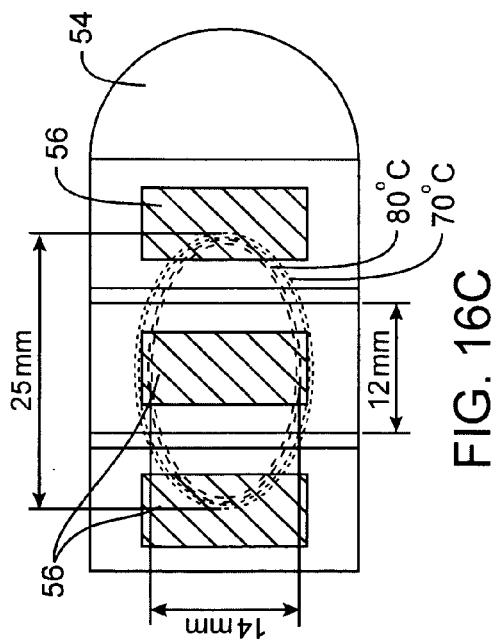

To provide the enhanced treatment width with a cooled-electrode vaginal probe 54, a variety of electrode 56 configurations might be employed as illustrated in FIGS. 16A-16D. Such non-invasive probes may have electrodes having lateral widths relative to an axis of the probe of greater than 20 mm, with at least one (and often all) of the individual electrodes having a length of less than 8 mm as illustrated in FIGS. 16B and 16D. Three or more electrodes may be included, with the inner electrode(s) optionally being narrower than the outer electrodes so as to generate a laterally elongate treatment zone 55. In some embodiments, a single pair of electrodes may be used, as seen in the "proximal heating only" embodiment of FIG. 16A. Optionally, only a distal pair of electrodes may be used for heating. FIGS. 16B and 16D illustrate more compact positioning of the electrodes 56 as compared to FIGS. 16A and 16C. Moreover, FIG. 16B shows 3 mm wings.

Figure 17:
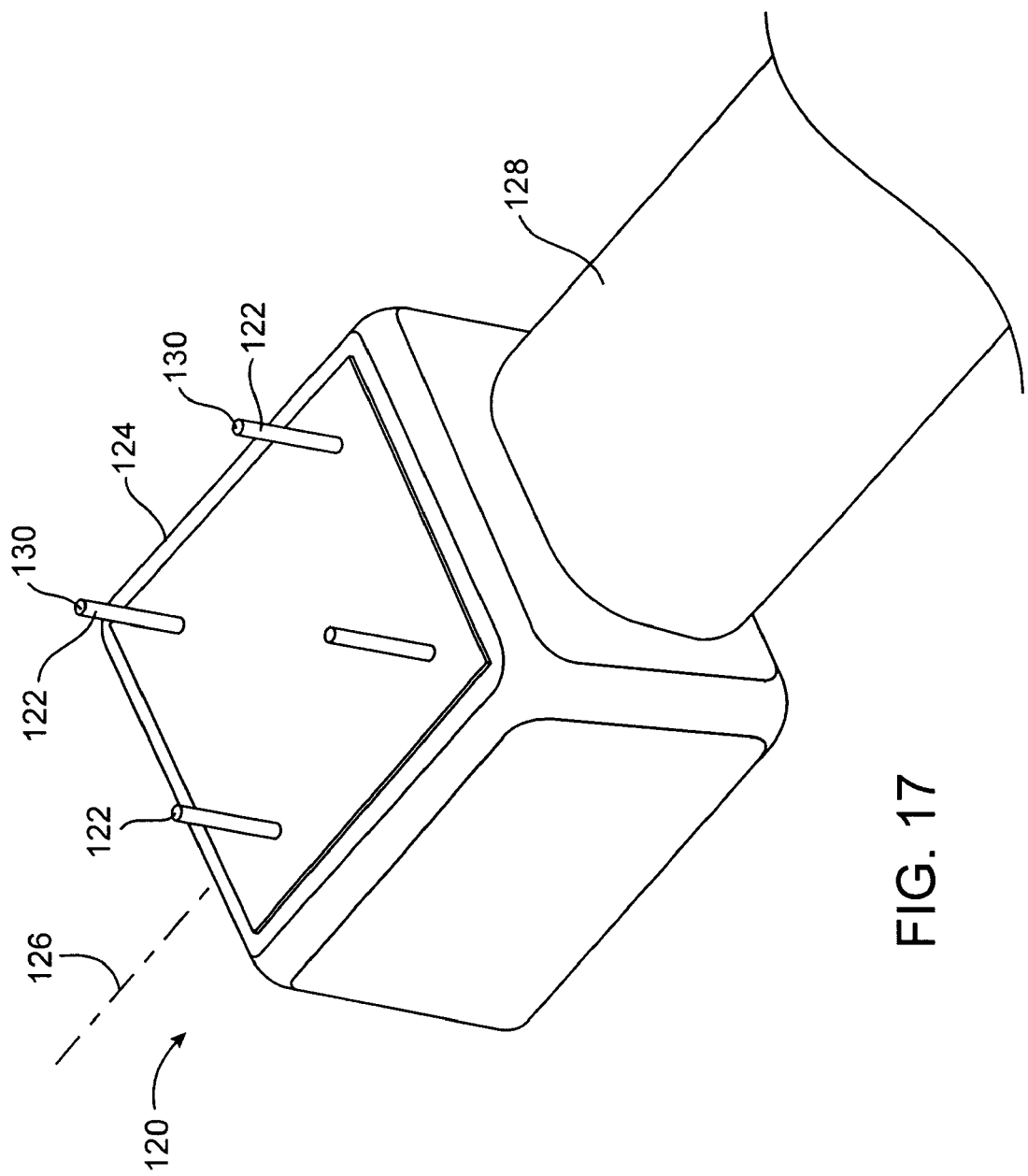
FIG. 17 illustrates a probe having tissue-penetrating electrodes for treating target volumes directly or through an intermediate tissue.

Still further alternative non-surgical probes might be employed to produce the desired treatment volumes. Referring now to FIG. 17, a distal portion of a needle probe 120 includes an array of needles 122 that can be advanced laterally relative to a probe and/or insertion axis 126 from a probe body 124. Body 124 generally defines a probe axis and has a size and shape suitable for axial insertion into the vagina. Probe 120 may optionally be finger supported rather than having an elongate handle 128 for manipulation and positioning. Needles 122 may have distal ends 130 suitable for penetrating tissue, and a proximal portion adjacent probe body 124 when the needles are in the extended position. The proximal portion may be electrically insulating, while at least a portion of the needle distal of the proximal portion is electrically conductive for transmitting RF energy, often in a bipolar mode between needles. Monopolar needle array of probes may also be used, as described above.

To facilitate penetrating the vaginal wall and placement of the distal conductive portion via needles within the target tissue, needles 122, the needle deployment mechanism, or body 124 may include a needle penetration depth verifier. For example, where vacuum ports may be disposed in body 124 along the tissue-engaging surface so as to promote engagement between the probe body 124 and the intermediate tissue when needles 122 are advanced, similar to the arrangement described in U.S. Pat. No. 6,325,798, the full disclosure of which is incorporated herein by reference. Optionally, to verify the insertion depth, needles 122 may have three positions relative to probe body 124. In a first position, the needles are disposed within the probe for probe positioning. In the second position, needles 122 and the proximal insulated portion of the needles extend from the probe body such that the needles are properly positioned for treatment of the desired treatment volume when the tissue engages the adjacent surface of probe 124. In the third position, needles 122 may extend significantly beyond this desired treatment needle depth. Advantageously, after the probe is inserted in position with the needles in the stowed position, they can be advanced to the extended position while the probe body 124 is held substantially against the intermediate tissue. Once the needles are fully extended into the tissue, even if advancement of the needles has pulled a portion of the intermediate tissue surface away from probe body 124, retracting of the needles 122 back part way into the probe body to ensure that the intermediate tissue surface firmly engages the probe body around needles 122, and the needles are positioned at the desired depth within the intermediate and target tissues. This overextension and partial retraction of the needles was described for deployment of a temperature sensing needle in U.S. patent application Ser. No. 10/211,973, as filed on Aug. 1, 2002, the full disclosure of which is incorporated herein by reference.

Figure 18C:
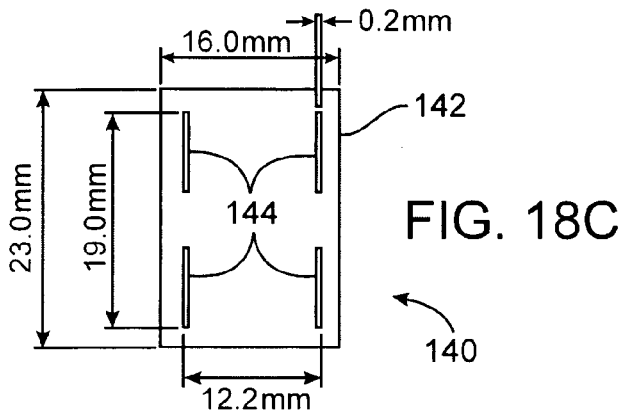
FIGS. 18A-18C illustrate an alternative probe having tissue-penetrating planar electrodes for direct surgical treatments of the endopelvic fascia.
Figure 18A:
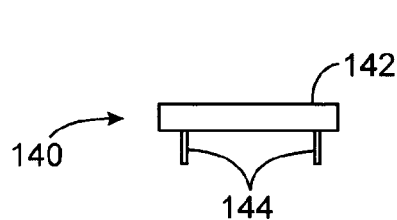
Figure 18B:
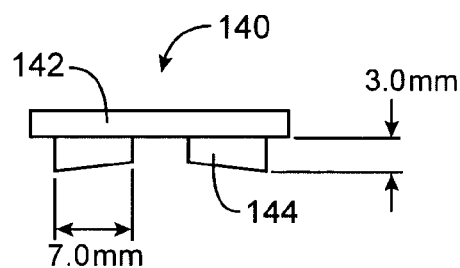

FIGS. 18A-18C illustrate side, end, and top views of an alternative treatment probe 140 having a probe body 142 supporting a plurality of planar or blade electrodes 144. Planar electrodes can be, but are not necessarily perfectly flat. These electrode structures may have major surfaces coupled by at least one edge, which may optionally be sharpened to function as a blade during insertion. Electrodes 144 are used as tissue-penetrating electrodes that may range in length from 2 to 10 mm, and are shown in FIG. 18B having lengths of about 3 mm. Directly engaging probe body 140 against the endopelvic fascia and pressing electrodes 144 into this target tissue would allow treatment by energizing the electrodes with bipolar (or monopolar) RF energy as described above. Bipolar energy might be driven between offset parallel planar electrodes, and a portion of the electrodes (such as the edges of the electrodes and/or the outer surface of the electrodes) may be insulated to limit edge-induced heat concentration, heat beyond the probe body footprint, and the like. While flat planar electrodes are shown, similar embodiments with curved electrodes may also make use of similar structures.

When used with a transvaginal incision such as that illustrated in FIG. 2, the proximal portion of electrodes 144 need not be insulated. Alternatively, particularly when the electrodes are used to penetrate through the intervening vaginal wall and into the endopelvic fascia, a proximal portion of the electrodes may be insulated, with the electrodes preferably having a three-position mechanism to help ensure accurate depth of the energized electrode portion. Such embodiments may include insulating material along at least the portion of electrodes 144 adjacent probe body 142, the insulated portion often extending a distance of between 1 and 5 mm from the probe body, typically extending at least about 2 mm from the probe body. As in each of the probes, a temperature sensor such as thermocouple may be disposed between bipolar tissue-penetrating needles or attached to an insulated portion of the tissue-penetrating electrode. Applying bipolar RF potential between the offset pairs of planar electrodes should promote even heating of the target tissue disposed therebetween.

Figure 19B:
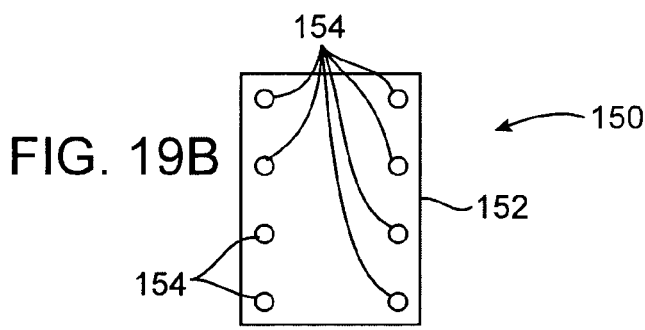
FIG. 19A and 19B illustrate an alternative probe having tissue-penetrating needle electrodes for non-surgical treatments of the endopelvic fascia.
Figure 19A:
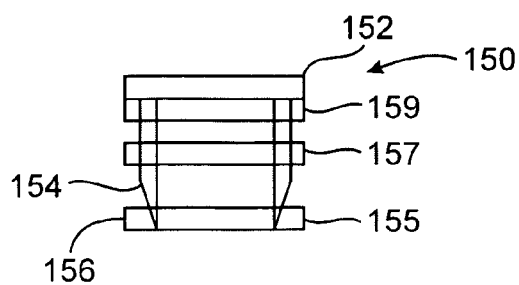

FIGS. 19A and 19B illustrate a side and top view of a needle array probe 150 having a body 152 from which an array of (16 gauge) needles 154 can extend. In this embodiment, a surface supported by a platen 156 of probe body 152 may be disposed at three positions relative to needles 154 so as to provide the variable needle extension configurations described above. The platen may be coupled to the remainder of the probe with a three-position cam arrangement, (optionally similar to a ball-point pen retracting system) or the like. At a packaged position 155, the needles are disposed within the probe body, with the tissue-engaging surface of platen 156 is positioned at or beyond distal ends of the needles so that the probe may be handled and positioned safely. At a treatment position 157, needles 154 extend about 5 to 6 mm beyond the platen. At this treatment position 157, 3 to 4 mm of the needles adjacent the tissue-engaging surface of the platen and probe body are insulated, while about 2 mm of needles 154 adjacent the needle distal ends are conductive and energized for heating tissue. This allows a good safety zone to avoid lesions and burning of the tissue surface engaged by the probe body. The platen at a maximum penetration position 159 allows the needles to extend well beyond the treatment position into the tissue, helping to avoid gaps between the probe body and intervening tissue when the needles are retracted to the treatment position as described above.

In some embodiments, the tissue-penetrating electrodes may include heat extractors to avoid tissue ablation adjacent the electrodes. Such tissue ablation may result in separation of the electrode surface from the tissue, increasing impedance and effectively ending treatment prematurely. Optionally, the needles may have an internal flow path or port for delivery of cooled saline, deionized water, or the like to an interior surface of the needle. This cooling fluid may be directed toward the distal portion of an internal lumen within the needle near the sharpened tip, but may not inject saline into the tissue. In other embodiments, a conductive fluid such as saline may be delivered through the needle and into the adjoining tissue, either for use as a cooling fluid or as a "wet electrode" to expand the effective treatment size. Cooling may optionally be effected by cryogenic cooling of the probe body and/or electrodes. As illustrated in FIG. 21C, expandable electrodes formed of a deformable material such as a shape-memory alloy may expand during heating so as to follow the tissue as it recedes adjacent to the electrode surface. In the exemplary embodiment, a two part electrode 180 is pulled together 182 when cold for insertion. Heating of the tissue and electrode 180 causes a shape memory alloy of the electrode to expand 184 against the tissue so as to maintain contact with the tissue.

Figure 20A:
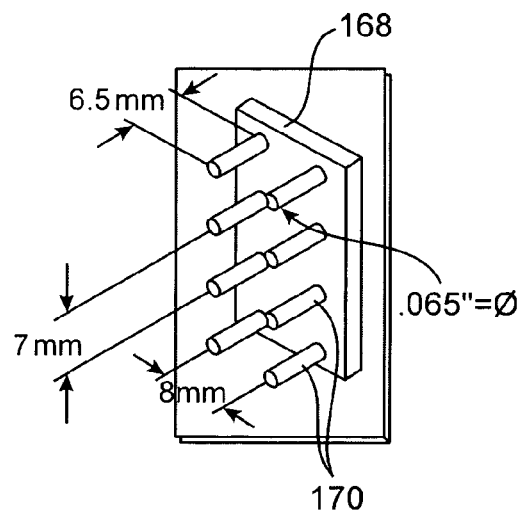
FIGS. 20A-20D illustrate further alternative probes having tissue-penetrating electrodes.
Figure 20B:
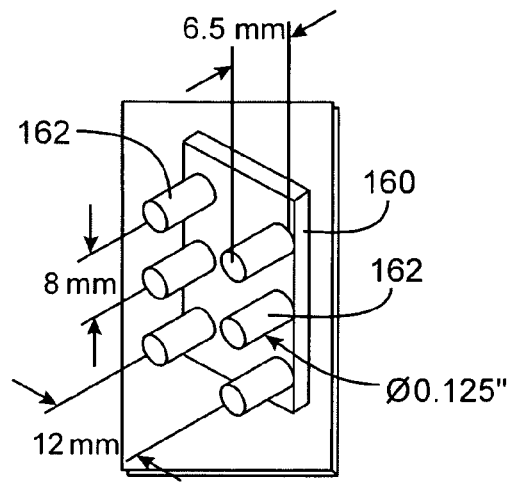
Figure 20C:
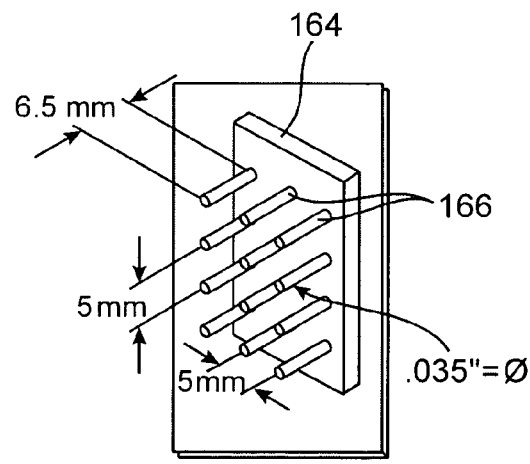
Figure 20D:
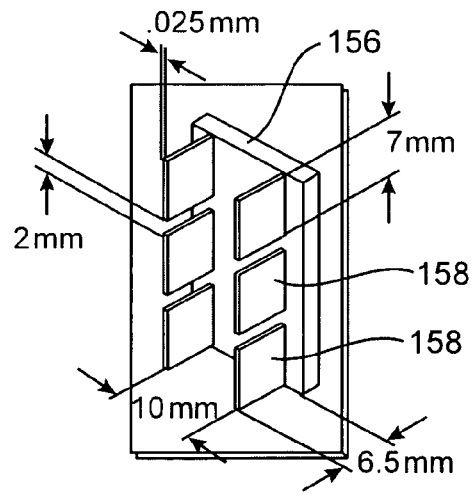

Appropriate sizes, spacings, and numbers of tissue-penetrating electrodes may be determined from experiments similar to those noted above. A wide variety of probe configurations might be employed. A probe 156 illustrated in FIG. 20D may heat a target region having a length of 15 mm and a width of 25 mm with an array of 6 planar electrodes 158, each active electrode being roughly 7 mm by 2-8 mm (optionally being 2 or 6.5 mm) by 0.25 mm. The pairs of electrodes can be spaced by about 10 mm, and may be capable of providing a treatment volume of 633 cubic millimeters heated to at least 70 C for at least 30 seconds. As illustrated in FIG. 20B, a probe 160 having 0.125" OD needle electrodes 162 spaced at 12 mm might instead produce a treatment volume of 712 cubic millimeters when heating the same region. Needles having smaller diameters will generally be in closer pairs. The probe 164 of FIG. 20C has smaller 20 gauge (0.035" OD) needles 166, and may include 12 electrodes separated by 5 mm to generate the same region in two separate treatments (at least one middle electrode optionally being used as return electrode for two adjacent electrodes, with the middle electrode optionally being slightly larger to accommodate the greater current density), while a probe 168 of FIG. 20A having 16 gauge (0.065" OD) needles 170 may include 8 electrodes spaced at 8 mm.

Still further tissue-penetrating electrode configuration alternatives are possible. Along with vacuum systems and over-insertion/retraction arrangements to verify insertion depth, "C" shaped needles or corkscrew-shaped needles might also be employed. As illustrated in FIGS. 21A and B, "C" shaped curved electrodes 172 (or inwardly angled straight penetrating electrodes) may be advanced distally from a probe body 174 into a tissue 176 so that distal portions of an electrode pair are closer than proximal electrode portions. This allows treatment volumes 178 to be heated while inhibiting injury to an intervening tissue, optionally without insulating the proximal electrodes, due to the higher proximal impedance from the greater separation. To inhibit tissue ablation or desiccation adjacent tissue-penetrating electrodes, rotating the needle, vibrating the needle, or slowly advancing the needle if an impedance rise is observed during treatment may be beneficial.

Combinations of elements from the above probes can also be used. For example, as shown in FIGS. 22A and 22B, one or more tissue-penetrating electrode needles (16 gauge) 186 may extend from a probe body surface 188 having one or more cooled surface electrodes 190. As shown, needle 186 may have an insulated proximal portion 192 comprising a PE, PI, or epoxy coating or alternatively be coupled to a small insulator ring to achieve electrical isolation. The surface electrodes 190 (and optionally, penetrating electrodes) may be cooled cryogenically, with cooled fluid or the like. Where the tissue-penetrating electrode 186 is both electrically isolated from and thermally coupled to the cooled surface electrode 190, ablation of tissue adjacent the penetrating electrode surface may be inhibited by a lower penetrating electrode surface temperature. Such surface electrodes 190 may also be used to reduce the number of tissue-penetrating electrodes 186 for a given treatment volume.

Referring now to FIG. 23, the development of treatment volume at a temperature of above 70° C. (left legend) as a function of dwell time is graphically illustrated. A non-invasive cooled electrode probe similar to that shown in FIGS. 6 and 6A heats tissue until the temperature sensing needle at 4.5 mm depth reaches a set point of 75° C. at 185 seconds. Following this set point, the RF energy is lowered and a dwell time of 45 seconds is maintained. The RF energy is then turned off at 230 seconds. The heat then remains for about 15 seconds after this point, to about 245 seconds. If the RF energy was turned off at the set point 185 seconds (i.e., no dwell time), the treatment volume of tissue above 70° C. between about 170 and 200 seconds would have been less than 70 cubic millimeters. In contrast, as shown in FIG. 23, the treatment volume of tissue above 70° C. between about 215 and 245 seconds is greater than 300 cubic millimeters, a four-fold increase over heating with no dwell period. Hence, dwell periods may play an important role in achieving increased treatment tissue volume.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. Therefore, the above description should not be taken as limiting the scope of the invention which is defined by the appended claims.

What is claimed is:

1. A method for treating incontinence, the method comprising: aligning a probe body with a collagenous pelvic tissue; heating a treatment volume of at least 100 cubic millimeters of the collagenous tissue using the aligned probe body.

2. The method of claim 1, wherein the treatment volume is separated from a urethra by at least about 1 cm.

3. The method of claim 2, wherein the treatment volume is offset laterally from the urethra to a right side or left side.

4. The method of claim 2, wherein the treatment volume comprises at least 300 cubic millimeters of collagenous tissue, wherein the heating is performed so that the treatment volume is heated to a temperature of at least 70° C. for a time of at least 30 seconds, wherein the treatment volume is offset laterally from the urethra to a right side of a patient, and further comprising heating another treatment volume offset laterally from the urethra to a left side of the patient, the other treatment volume comprising at least 300 cubic millimeters of collagenous tissue and heated to at least 70° C. for at least 30 seconds.

5. The method of claim 1, wherein the treatment volume is heated to at least about 65° C. for at least about 100 seconds.

6. The method of claim 1, wherein the treatment volume is heated to at least about 75° C. for at least about 10 seconds.

7. The method of claim 1, further comprising applying a dwell time after a desired heating temperature is achieved so as to increase treatment tissue volume.

8. The method of claim 1, wherein the treatment volume has a length orientation extending along a urethra, a depth orientation extending between the collagenous tissue and the probe body, and a width that is greater than the length of the treatment volume.

9. The method of claim 1, wherein the treatment volume has a length orientation extending along a urethra, a depth orientation extending between the collagenous tissue and the probe body, and a width that is less than the length of the treatment volume.

10. The method of claim 1, further comprising registering a position of the treatment volume along an axis of the urethra with reference to a guide body disposed within the urethra.

11. The method of claim 1, further comprising registering a position of the treatment volume with reference to bone.

12. The method of claim 1, wherein the probe is aligned so that an intermediate tissue is disposed between the probe body and the treatment volume.

13. The method of claim 12, wherein the treatment volume comprises tissue separated from the aligned probe body by a distance within a range of about 2 to 8 mm.

14. The method of claim 12, wherein the treatment volume comprises tissue separated from the aligned probe body by a distance within a range of about 2 to 4 mm.

15. The method of claim 12, wherein the heating is performed so as to inhibit necrosis of the intermediate tissue.

16. The method of claim 15, wherein the heating is performed while cooling the intermediate tissue.

17. The method of claim 15, wherein the heating is performed without cooling of the intermediate tissue.

18. The method of claim 1, wherein the heating is performed by tip movement of at least a pair of electrodes supported by the probe body.

19. The method of claim 18, wherein the treatment volume increases as the tip movement speed decreases.

20. The method of claim 1, wherein the treatment volume comprises at least 300 cubic millimeters of collagenous tissue.

* * * * *

UNITED STATES PATENT AND TRADEMARK OFFICE
CERTIFICATE OF CORRECTION

PATENT NO.         : 7,315,762 B2                                      Page 1 of 1
APPLICATION NO. : 10/759732
DATED              : January 1, 2008
INVENTOR(S)        : Oren A. Mosher et al.

It is certified that error appears in the above-identified patent and that said Letters Patent is hereby corrected as shown below:

Title Page

Item (73) Delete "American Medical Systems, Inc." and insert --AMS RESEARCH

CORPORATION--

Signed and Sealed this

Third Day of March, 2009

JOHN DOLL
*Acting Director of the United States Patent and Trademark Office*